(12) United States Patent
Shandas et al.

(10) Patent No.: US 10,828,218 B2
(45) Date of Patent: Nov. 10, 2020

(54) SURGICAL TABLE AND ACCESSORIES TO FACILITATE HIP ARTHROSCOPY

(71) Applicant: Stryker Corporation, Kalamazoo, MI (US)

(72) Inventors: Robin Shandas, Denver, CO (US); Omer Yehezkel Mei-Dan, Denver, CO (US); Jacob Segil, Denver, CO (US); Jennifer Wagner, Denver, CO (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/728,876

(22) Filed: Dec. 27, 2019

(65) Prior Publication Data

US 2020/0129356 A1    Apr. 30, 2020

Related U.S. Application Data

(60) Division of application No. 16/197,913, filed on Nov. 21, 2018, which is a continuation of application No.
(Continued)

(51) Int. Cl.
*A61G 13/00* (2006.01)
*A61G 13/08* (2006.01)
(Continued)

(52) U.S. Cl.
CPC .......... *A61G 13/0081* (2016.11); *A61G 13/04* (2013.01); *A61G 13/08* (2013.01);
(Continued)

(58) Field of Classification Search
CPC ...... A61G 7/07; A61G 13/0081; A61G 13/04; A61G 13/08; A61G 13/1225;
(Continued)

(56) References Cited

U.S. PATENT DOCUMENTS 2,150,314 A    3/1939 Bell
D130,079 S    10/1941 Weller
(Continued)

FOREIGN PATENT DOCUMENTS

DE    10 2005 023 477    11/2006
DE    20 2009 003 314    7/2009
(Continued)

OTHER PUBLICATIONS

Hip Distraction System: Advanced solutions for supine hip arthroscopy procedures, Arthrex, 2013, pp. 1-6.
(Continued)

*Primary Examiner* — Nicholas F Polito
(74) *Attorney, Agent, or Firm* — Pandiscio & Pandisciso

(57) ABSTRACT

Embodiments disclosed herein concern a distraction system for use with a surgical table having a table portion and a base portion. The distraction system includes a pair of arms rotatably connectable to the base portion at a proximal end portion of each arm. A pair of telescopically adjustable support posts extend upwardly from corresponding arms. Each arm rotates about a vertically oriented axis to provide for hip adduction and abduction of a patient's leg. Each support post extends from a linear bearing attached to the corresponding one of the pair of arms for movement along the aim to facilitate applying traction to a patient's leg. The system can also include a table extension attachable to the table portion and a friction pad mounted on the table extension.

23 Claims, 31 Drawing Sheets

Related U.S. Application Data

15/579,409, filed as application No. PCT/US2016/036090 on Jun. 6, 2016.

(60) Provisional application No. 62/171,891, filed on Jun. 5, 2015, provisional application No. 62/250,072, filed on Nov. 3, 2015.

(51) Int. Cl.
*A61G 13/12* (2006.01)
*A61G 13/10* (2006.01)
*A61B 17/02* (2006.01)
*A61G 13/04* (2006.01)

(52) U.S. Cl.
CPC ....... *A61G 13/101* (2013.01); *A61G 13/1245* (2013.01); *A61B 2017/0275* (2013.01)

(58) Field of Classification Search
CPC .. A61G 13/123; A61G 13/126; A61G 13/101; A61G 13/1245; A61B 2017/0275
See application file for complete search history.

(56) References Cited

U.S. PATENT DOCUMENTS

| | | |
|---|---|---|
| D171,677 S | 3/1954 | Adler |
| 3,220,022 A | 11/1965 | Nelson |
| D221,035 S | 6/1971 | Raines et al. |
| 3,745,996 A | 7/1973 | Rush, Sr. |
| D264,531 S | 5/1982 | Trode |
| 4,708,510 A | 11/1987 | McConnell et al. |
| 4,865,303 A | 9/1989 | Hall |
| 5,162,039 A | 11/1992 | Dahners |
| 5,287,575 A | 2/1994 | Allen et al. |
| 5,306,231 A | 4/1994 | Cullum et al. |
| 5,560,577 A | 10/1996 | Keselman |
| 5,582,379 A | 12/1996 | Keselman et al. |
| 5,608,934 A * | 3/1997 | Torrie ................ A61G 13/0036 5/624 |
| D385,040 S | 10/1997 | Keselman |
| D387,581 S | 12/1997 | Parker et al. |
| 5,702,389 A | 12/1997 | Taylor et al. |
| D389,580 S | 1/1998 | Keselman et al. |
| 5,728,095 A | 3/1998 | Taylor et al. |
| 5,918,330 A | 7/1999 | Navarro et al. |
| 5,971,984 A | 10/1999 | Taylor et al. |
| 6,109,625 A | 8/2000 | Hewitt |
| 6,162,223 A | 12/2000 | Orsak et al. |
| 6,286,164 B1 | 9/2001 | Lamb et al. |
| 6,678,908 B2 | 1/2004 | Borders et al. |
| D546,599 S | 7/2007 | Goldberg |
| 7,237,556 B2 | 7/2007 | Smothers et al. |
| 7,337,483 B2 | 3/2008 | Boucher et al. |
| 7,343,635 B2 | 3/2008 | Jackson |
| 7,477,926 B2 | 1/2009 | McCombs |
| 7,520,007 B2 | 4/2009 | Skripps |
| 7,520,008 B2 | 4/2009 | Wong et al. |
| 7,565,708 B2 | 7/2009 | Jackson |
| 7,572,292 B2 | 8/2009 | Crabtree et al. |
| 7,600,281 B2 | 10/2009 | Skripps |
| 7,669,262 B2 | 3/2010 | Skripps et al. |
| 7,677,249 B2 | 3/2010 | Kong et al. |
| 7,739,762 B2 | 6/2010 | Lamb et al. |
| RE41,412 E | 7/2010 | Van Steenburg |
| 7,762,975 B2 | 7/2010 | Memminger |
| 7,832,401 B2 | 11/2010 | Torrie et al. |
| 7,862,570 B2 | 1/2011 | Russell et al. |
| 7,878,992 B2 | 2/2011 | Mitsuishi et al. |
| 7,882,583 B2 | 2/2011 | Skripps |
| 7,947,006 B2 | 5/2011 | Torrie et al. |
| 7,949,006 B2 | 5/2011 | Jagadesan et al. |
| 7,949,386 B2 | 5/2011 | Buly et al. |
| 7,979,932 B2 | 7/2011 | Liang |
| 8,011,045 B2 | 9/2011 | Skripps |
| 8,037,884 B2 | 10/2011 | Weinstein et al. |
| 8,055,487 B2 | 11/2011 | James |
| 8,060,960 B2 | 11/2011 | Jackson |
| 8,109,942 B2 | 2/2012 | Carson |
| 8,152,816 B2 | 4/2012 | Tuma et al. |
| D665,912 S | 8/2012 | Skripps |
| 8,234,730 B2 | 8/2012 | Skripps |
| 8,234,731 B2 | 8/2012 | Skripps |
| 8,256,050 B2 | 9/2012 | Wong et al. |
| 8,281,434 B2 | 10/2012 | Skripps |
| 8,322,342 B2 | 12/2012 | Soto et al. |
| 8,388,553 B2 | 3/2013 | James et al. |
| 8,397,323 B2 | 3/2013 | Skripps et al. |
| 8,413,660 B2 | 4/2013 | Weinstein et al. |
| 8,464,720 B1 | 6/2013 | Pigazzi et al. |
| 8,469,911 B2 | 6/2013 | Hiebert |
| 8,486,070 B2 | 7/2013 | Morgan et al. |
| 8,491,597 B2 | 7/2013 | Russell et al. |
| 8,491,664 B2 | 7/2013 | McMahon et al. |
| 8,511,314 B2 | 8/2013 | Pigazzi et al. |
| 8,545,570 B2 | 10/2013 | Crabtree et al. |
| 8,555,439 B2 | 10/2013 | Soto et al. |
| 8,570,187 B2 | 10/2013 | Janna et al. |
| 8,611,697 B2 | 12/2013 | Nathaniel et al. |
| 8,679,187 B2 | 3/2014 | Allen et al. |
| 8,690,806 B2 | 4/2014 | Hiebert |
| 8,690,807 B2 | 4/2014 | Hiebert |
| 8,702,712 B2 | 4/2014 | Jordan et al. |
| 8,707,484 B2 | 4/2014 | Jackson et al. |
| 8,707,486 B2 | 4/2014 | Chella et al. |
| 8,719,979 B2 | 5/2014 | Jackson |
| 8,721,643 B2 | 5/2014 | Morgan et al. |
| 8,795,312 B2 | 8/2014 | Fan et al. |
| 8,806,679 B2 | 8/2014 | Soto et al. |
| 8,826,474 B2 | 9/2014 | Jackson |
| 8,826,475 B2 | 9/2014 | Jackson |
| 8,828,009 B2 | 9/2014 | Allen et al. |
| 8,833,707 B2 | 9/2014 | Steinberg et al. |
| 8,839,471 B2 | 9/2014 | Jackson |
| 8,844,077 B2 | 9/2014 | Jackson et al. |
| 8,845,568 B2 | 9/2014 | Clark et al. |
| 8,856,986 B2 | 10/2014 | Jackson |
| 8,890,511 B2 | 11/2014 | Belew |
| 8,893,333 B2 | 11/2014 | Soto et al. |
| 8,894,716 B2 | 11/2014 | McMahon et al. |
| 8,938,826 B2 | 1/2015 | Jackson |
| 8,944,065 B2 | 2/2015 | Slusarz, Jr. |
| 8,945,026 B2 | 2/2015 | Moser et al. |
| 8,978,180 B2 | 3/2015 | Jackson |
| 8,986,228 B2 | 3/2015 | Auchinleck et al. |
| 8,997,284 B2 | 4/2015 | Kreuzer et al. |
| 8,997,286 B2 | 4/2015 | Wyslucha et al. |
| 8,997,749 B2 | 4/2015 | Drake et al. |
| 9,056,012 B2 | 6/2015 | Crabtree, Jr. et al. |
| 9,072,646 B2 | 7/2015 | Skripps et al. |
| 9,085,915 B1 | 7/2015 | Emmett |
| 9,101,393 B2 | 8/2015 | Jordan et al. |
| 9,107,792 B2 | 8/2015 | Catacchio et al. |
| 9,119,610 B2 | 9/2015 | Matta et al. |
| 9,161,875 B2 | 10/2015 | Clark et al. |
| 9,161,876 B2 | 10/2015 | Pigazzi et al. |
| 9,173,649 B2 | 11/2015 | Clark et al. |
| 9,180,062 B2 | 11/2015 | Jackson |
| 9,186,291 B2 | 11/2015 | Jackson et al. |
| 9,198,817 B2 | 12/2015 | Jackson |
| 9,205,013 B2 | 12/2015 | Jackson |
| 9,211,223 B2 | 12/2015 | Jackson |
| 9,226,865 B2 | 1/2016 | Jackson |
| 9,233,043 B2 | 1/2016 | Labedz et al. |
| 9,265,679 B2 | 2/2016 | Jackson |
| 9,289,342 B2 | 3/2016 | Jackson |
| 9,295,433 B2 | 3/2016 | Jackson et al. |
| 9,295,556 B2 | 3/2016 | Perez, III et al. |
| 9,301,897 B2 | 4/2016 | Jackson |
| 9,308,145 B2 | 4/2016 | Jackson |
| 9,364,380 B2 | 6/2016 | Jackson |
| 9,456,945 B2 | 10/2016 | Jackson |
| 9,468,576 B2 | 10/2016 | Jackson |
| 9,510,987 B2 | 12/2016 | Jackson et al. |

(56) References Cited

U.S. PATENT DOCUMENTS

| | | | |
|---|---|---|---|
| 9,549,865 B2 | 1/2017 | Hiebert | |
| 9,610,206 B2 | 4/2017 | Jackson | |
| 9,672,662 B2 | 6/2017 | Scanlan et al. | |
| 9,750,656 B1 | 9/2017 | Pigazzi et al. | |
| 9,782,287 B2 | 10/2017 | Pigazzi et al. | |
| 9,931,262 B2 | 4/2018 | Pigazzi et al. | |
| 9,936,941 B2 | 4/2018 | Weisel et al. | |
| 9,949,883 B1 | 4/2018 | Pigazzi et al. | |
| 10,034,806 B1 | 7/2018 | Greenhalgh, Sr. | |
| D832,334 S | 10/2018 | Kushner et al. | |
| 10,130,542 B1 | 11/2018 | Strawder | |
| 10,159,520 B2 | 12/2018 | Krickeberg et al. | |
| 2002/0023298 A1 | 2/2002 | Lamb et al. | |
| 2004/0003468 A1 | 1/2004 | Mitsuishi et al. | |
| 2004/0092854 A1 | 5/2004 | D'Amico | |
| 2004/0133979 A1 | 7/2004 | Newkirk et al. | |
| 2004/0133983 A1 | 7/2004 | Newkirk et al. | |
| 2005/0160533 A1 | 7/2005 | Boucher et al. | |
| 2006/0074366 A1 | 4/2006 | Ryan et al. | |
| 2006/0100562 A1 | 5/2006 | Pamplin | |
| 2006/0130713 A1 | 6/2006 | Jones et al. | |
| 2006/0185090 A1 | 8/2006 | Jackson | |
| 2006/0271056 A1 | 11/2006 | Terrill-Grisoni et al. | |
| 2007/0277350 A1 | 12/2007 | Hines | |
| 2008/0216231 A1 | 9/2008 | Lambarth et al. | |
| 2011/0023893 A1 | 2/2011 | Striggow et al. | |
| 2011/0119829 A1 | 5/2011 | Skripps et al. | |
| 2011/0190676 A1 | 8/2011 | Torrie et al. | |
| 2012/0059376 A1 | 3/2012 | Rains et al. | |
| 2012/0073476 A1 | 3/2012 | Lai | |
| 2012/0204885 A1 | 8/2012 | Koch | |
| 2012/0233782 A1 | 9/2012 | Kreuzer et al. | |
| 2012/0240938 A1 | 9/2012 | Pamichev | |
| 2012/0255122 A1 | 10/2012 | Diel et al. | |
| 2012/0259261 A1 | 10/2012 | Clark et al. | |
| 2012/0259343 A1 | 10/2012 | Clark et al. | |
| 2013/0081635 A1 | 4/2013 | Drake et al. | |
| 2013/0111666 A1 | 5/2013 | Jackson | |
| 2013/0133137 A1 | 5/2013 | Jackson et al. | |
| 2013/0174853 A1* | 7/2013 | Pigazzi | A61G 13/122 128/845 |
| 2013/0191994 A1 | 8/2013 | Bellows et al. | |
| 2013/0199541 A1 | 8/2013 | Sluss et al. | |
| 2013/0269710 A1 | 10/2013 | Hight et al. | |
| 2013/0312187 A1 | 11/2013 | Jackson | |
| 2013/0312188 A1 | 11/2013 | Jackson | |
| 2013/0338792 A1 | 12/2013 | Schmieding et al. | |
| 2013/0345605 A1 | 12/2013 | Steele | |
| 2014/0020181 A1 | 1/2014 | Jackson | |
| 2014/0033434 A1 | 2/2014 | Jackson | |
| 2014/0068863 A1 | 3/2014 | Clark et al. | |
| 2014/0068866 A1 | 3/2014 | Catacchio et al. | |
| 2014/0082842 A1 | 3/2014 | Jackson | |
| 2014/0173827 A1* | 6/2014 | Hiebert | A61G 13/125/624 |
| 2014/0174451 A1 | 6/2014 | Hiebert | |
| 2014/0196212 A1 | 7/2014 | Jackson | |
| 2014/0201913 A1 | 7/2014 | Jackson | |
| 2014/0201914 A1 | 7/2014 | Jackson | |
| 2014/0208512 A1 | 7/2014 | Jackson | |
| 2014/0208513 A1 | 7/2014 | Hiebert | |
| 2014/0215718 A1 | 8/2014 | Wootton | |
| 2014/0222407 A1 | 8/2014 | Jordan et al. | |
| 2014/0309646 A1 | 10/2014 | Fan et al. | |
| 2014/0317847 A1 | 10/2014 | Jackson | |
| 2014/0324056 A1 | 10/2014 | Nikolchev et al. | |
| 2014/0359941 A1 | 12/2014 | Sharps et al. | |
| 2014/0366271 A1* | 12/2014 | Marshall | A61F 5/3776 5/621 |
| 2015/0008201 A1 | 1/2015 | Qiang et al. | |
| 2015/0059094 A1 | 3/2015 | Jackson | |
| 2015/0067985 A1 | 3/2015 | Gaenzle | |
| 2015/0122268 A1 | 5/2015 | Slusarz, Jr. | |
| 2015/0150743 A1 | 6/2015 | Jackson | |
| 2015/0164724 A1 | 6/2015 | Drake et al. | |
| 2015/0196447 A1 | 7/2015 | Henderson et al. | |
| 2015/0202106 A1 | 7/2015 | Hight et al. | |
| 2015/0231013 A1 | 8/2015 | Bernardoni et al. | |
| 2015/0238273 A1 | 8/2015 | Jordan et al. | |
| 2015/0238380 A1 | 8/2015 | Kreuzer et al. | |
| 2015/0245915 A1 | 9/2015 | Crabtree, Jr. et al. | |
| 2015/0245969 A1 | 9/2015 | Hight et al. | |
| 2015/0245971 A1 | 9/2015 | Bernardoni et al. | |
| 2015/0272681 A1 | 10/2015 | Skripps et al. | |
| 2015/0297435 A1* | 10/2015 | Visco | A61G 13/1245 128/876 |
| 2015/0342813 A1 | 12/2015 | Catacchio et al. | |
| 2015/0366622 A1 | 12/2015 | Wyslucha et al. | |
| 2016/0008201 A1 | 1/2016 | Jackson et al. | |
| 2016/0038364 A1 | 2/2016 | Jackson | |
| 2016/0051432 A1 | 2/2016 | Clark et al. | |
| 2016/0067135 A1 | 3/2016 | Pigazzi et al. | |
| 2016/0095784 A1 | 4/2016 | Catacchio et al. | |
| 2016/0095785 A1 | 4/2016 | Catacchio et al. | |
| 2016/0106612 A1 | 4/2016 | Clark et al. | |
| 2016/0120720 A1 | 5/2016 | Hirsch | |
| 2016/0120726 A1 | 5/2016 | Moriarty et al. | |
| 2016/0184154 A1 | 6/2016 | Lafleche et al. | |
| 2016/0228281 A1 | 8/2016 | Marshall et al. | |
| 2016/0279007 A1* | 9/2016 | Flatt | A61G 13/126 |
| 2016/0317237 A1 | 11/2016 | Geiger | |
| 2016/0338691 A1 | 11/2016 | Weber et al. | |

FOREIGN PATENT DOCUMENTS

| | | |
|---|---|---|
| DE | 20 2012 101 347 | 8/2012 |
| DE | 10 2011 016 456 | 2/2016 |
| EP | 2 574 325 | 4/2013 |
| EP | 2 623 082 | 8/2013 |
| EP | 2 618 313 | 7/2014 |
| EP | 2 873 405 | 5/2015 |
| EP | 2 982 880 | 2/2016 |
| EP | 2 802 305 | 10/2018 |
| WO | WO 2003/061544 | 7/2003 |
| WO | WO 2008/091239 | 8/2006 |
| WO | WO 2007/021806 | 2/2007 |
| WO | WO 2007/080454 | 7/2007 |
| WO | WO 2008/150731 | 12/2008 |
| WO | WO 2009/062324 | 5/2009 |
| WO | WO 2013/034916 | 3/2013 |
| WO | WO 2014/043538 | 3/2014 |
| WO | WO 2014/045194 | 3/2014 |
| WO | WO 2014/045199 | 3/2014 |
| WO | WO 2014/153329 | 9/2014 |
| WO | WO 2014/205218 | 12/2014 |
| WO | WO 2016/197142 | 12/2016 |

OTHER PUBLICATIONS

Opfell, A., Hip Arthroscopy & Fracture Kit: Maximize patient safety during arthroscopic hip procedures, Xodus Medical, Jul. 12, 2018.

The Pink Hip Kit SN: Postless Positioning System—H1P40614SN, Xodus Medical, 2019, https://www.xodusmeclical.com/Product/HIP40614SN.

Terry, M.A., Arthroscopic Hip Patient Positioning Using the Advanced Supine Hip Positioning System: Hip Technique Guide, Smith & Nephew, 2013, pp. 1-8.

Mei-Dan, O. et al. Hip Arthroscopy Distraction Without the Use of Perineal Post: Prospective Study (Abstract), vol. 36, No. 1, Jan. 2013, pp. e1-e5.

Young, D.A. et al., Technique aows for hip arthoscopy distraction without perineal post, Orthopedics Today, Jun. 2013, https://www.heallo.com/orthopedics/arthroscopy/news/print/orthopectics-today/%7Bac540b4c-9b43-4736-ae8a-606b1457af8b&7D/technique-allows-for--hip-arthroscopy-distraction-without-perineal-post.

Kollmorgen, Robert C., The Pink Hip Kit®: Postless Hip Arthroscopy Positioning System, Xodus Medical.

Pink Pad—Advanced Trendelenburg Positioning System, Xodus Medical Inc., 2018, https://www.xodusmedical.com/pinkpad.

(56) References Cited

OTHER PUBLICATIONS

The Pink Pad XL®: Advanced Trendelenburg Positioning System, Xodus Medical, 2018.
Steep Trendelenburg Positioners, Prime Medical LLC, 2019, http://primemedicalllc.com/steep-trendelenburg-positioners/.
Trendelenburg Positioning Kits, Soule Medical, 2019, https://www.soulemedical.com/index.php/trendelenburg-positioning-kit.

* cited by examiner

Patterned material for wrapping and securing arms

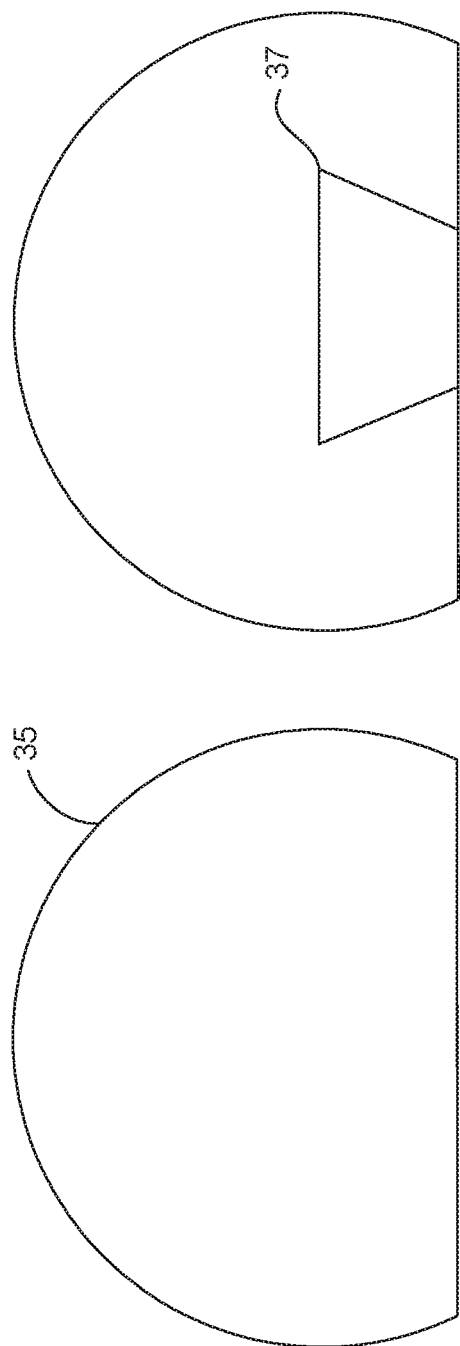
FIG. 7A
FIG. 7B
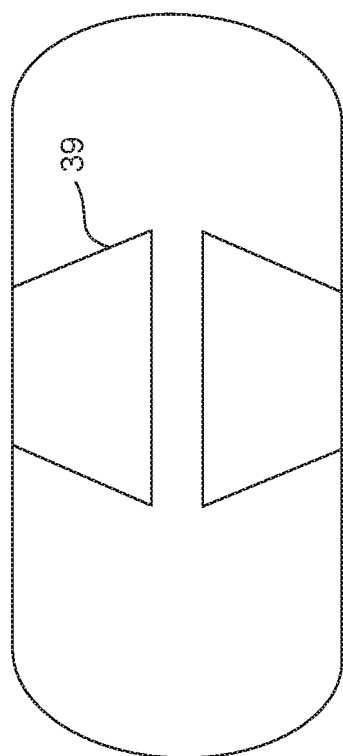
FIG. 7C

| Θ (degrees) | 15.00 | 15.00 | 15.00 | 15.00 | 15.00 | 15.00 |
|---|---|---|---|---|---|---|
| Θ (Radians) | 0.26 | 0.26 | 0.26 | 0.26 | 0.26 | 0.26 |
| Traction Force (lbf) | 150.00 | 150.00 | 150.00 | 150.00 | 150.00 | 150.00 |
| Traction Force (N) | 667.23 | 667.23 | 667.23 | 667.23 | 667.23 | 667.23 |
| Gravitational Constant m/s^2 | 9.81 | 9.81 | 9.81 | 9.81 | 9.81 | 9.81 |
| Weight (#) | 60.00 | 100.00 | 140.00 | 180.00 | 220.00 | 260.00 |
| Mass (kg) | 27.22 | 45.36 | 63.50 | 81.65 | 99.79 | 117.93 |
| Coefficient of Friction | 2.3202 | 1.2850 | 0.8413 | 0.5948 | 0.4379 | 0.3293 |
| 5 degrees | 2.42 | 1.42 | 0.99 | 0.75 | 0.60 | 0.49 |
| 10 degrees | 2.36 | 1.35 | 0.91 | 0.67 | 0.52 | 0.41 |
| 15 degrees | 2.32 | 1.28 | 0.84 | 0.59 | 0.44 | 0.33 |
| Weight | 60.00 | 100.00 | 140.00 | 180.00 | 220.00 | 260.00 |

SURGICAL TABLE AND ACCESSORIES TO FACILITATE HIP ARTHROSCOPY

REFERENCE TO PENDING PRIOR PATENT APPLICATIONS

This patent application is a division of prior U.S. patent application Ser. No. 16/197,913, filed Nov. 21, 2018 by Stryker Corporation for SURGICAL TABLE AND ACCESSORIES TO FACILITATE HIP ARTHROSCOPY, which patent application is a continuation of prior U.S. patent application Ser. No. 15/579,409, filed Dec. 4, 2017 by Stryker Corporation for SURGICAL TABLE AND ACCESSORIES TO FACILITATE HIP ARTHROSCOPY, which patent application in turn:

(i) is a 371 national stage entry of International (PCT) Patent Application No. PCT/US16/36090, filed Jun. 6, 2016 by THE REGENTS OF THE UNIVERSITY OF COLORADO, A BODY CORPORATE for SURGICAL TABLE AND ACCESSORIES TO FACILITATE HIP ARTHROSCOPY, which in turn claims benefit of:
  (a) prior U.S. Provisional Patent Application Ser. No. 62/171,891, filed Jun. 5, 2015 by The Regents of the University of Colorado, a body corporate for SURGICAL TABLE AND ACCESSORIES TO FACILITATE HIP ARTHROSCOPY; and
  (b) prior U.S. Provisional Patent Application Ser. No. 62/250,072, filed Nov. 3, 2015 by The Regents of the University of Colorado, a body corporate for SURGICAL TABLE AND ACCESSORIES TO FACILITATE HIP ARTHROSCOPY.

The above-identified patent applications are hereby incorporated herein by reference.

TECHNICAL FIELD

Various embodiments of the present technology generally relate to surgical tables and accessories. More specifically, some embodiments generally relate to surgical tables and accessories to facilitate hip arthroscopy.

BACKGROUND

Hip arthroscopy is a surgical procedure being used with increasing frequency as the understanding of arthroscopic management of groin pain improves. The diagnostic and therapeutic uses are numerous and most commonly directed at intraarticular cartilage and labral pathology. However, to access the hip joint arthroscopically, traction must be placed on the leg to allow the surgeon access to the hip joint. Hip arthroscopy can be performed in the supine or lateral position, typically with the leg in a boot and a padded post in the groin to act as countertraction. The padded post can be used to distract the femur from the acetabulum, or realign fractured fragments.

The use of the perineal post has resulted in a variety of complications. For example, complications related to traction may be related to the amount of pressure of the post on the groin and the length of time the pressure is applied. In many cases the surgery may last two or more hours. Examples of complications of traction attributed to the post include, but are not limited to, injury of tissues, nerves (e.g., perineal or pudendal neuropraxias), blood vessels and other structures in the groin area. Accordingly, reliable and consistent techniques and tools to reduce the potential for complications during hip arthroscopy are beneficial.

BRIEF DESCRIPTION OF THE DRAWINGS

Embodiments of the present technology are introduced herein may be better understood by referring to the following Detailed Description in conjunction with the accompanying drawings, in which like reference numerals indicate identical or functionally similar elements.

FIGS. 7A-7C are enlarged cross-sections of various linear slides that may be used in various embodiments of the present technology.

Figure 1:
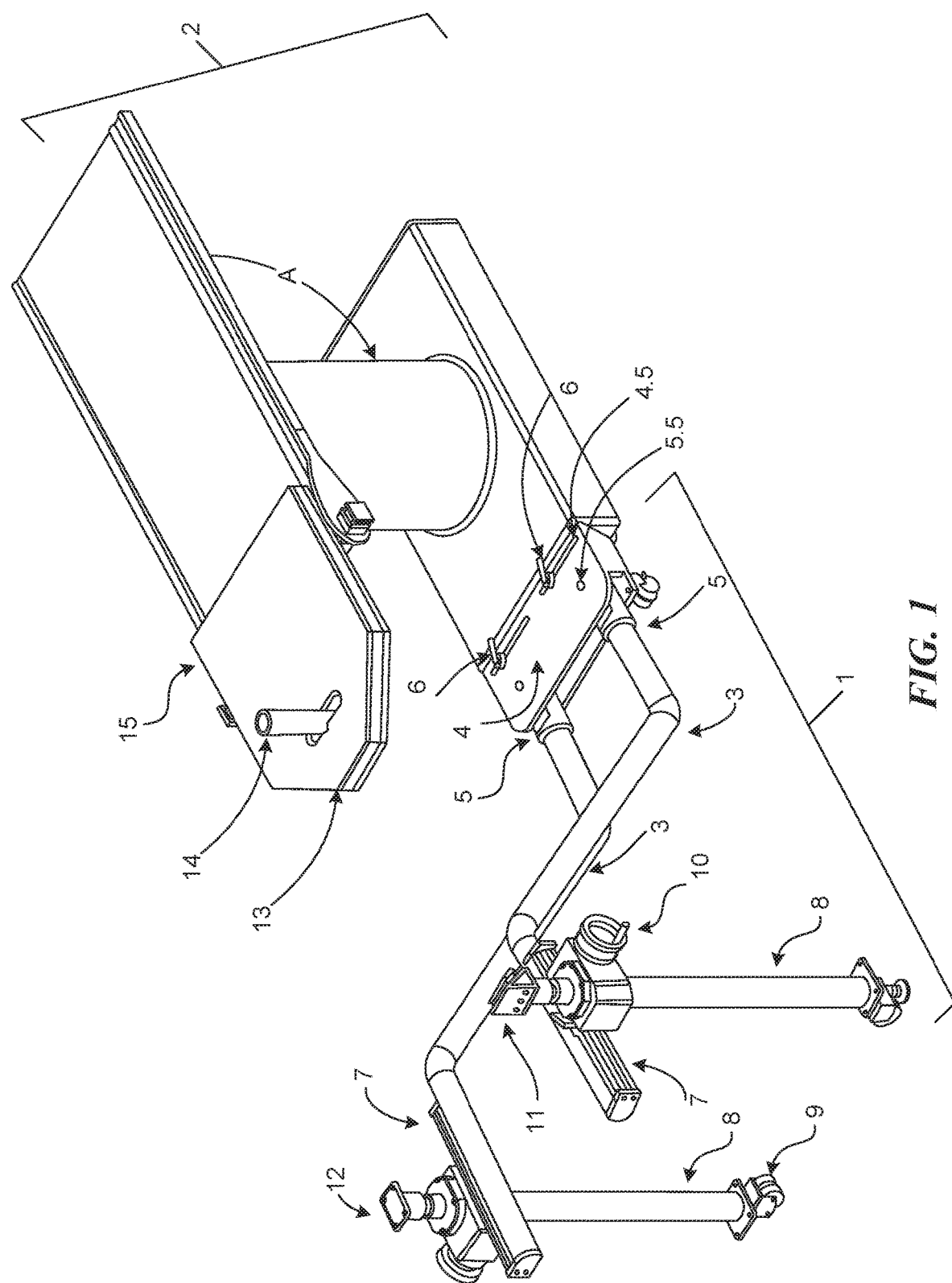
FIG. 1 is an isometric view of a surgical table and accessories in accordance with one or more embodiments of the present technology.

The headings provided herein are for convenience only and do not necessarily affect the scope or meaning of the claimed embodiments. Further, the drawings have not necessarily been drawn to scale. For example, the dimensions of some of the elements in the figures may be expanded or reduced to help improve the understanding of the embodiments. Moreover, while the disclosed technology is amenable to various modifications and alternative forms, specific embodiments have been shown by way of example in the drawings and are described in detail below. The intention, however, is not to limit the embodiments described. On the contrary, the embodiments are intended to cover all modifications, equivalents, and alternatives falling within the scope of the embodiments as defined by the appended claims.

DETAILED DESCRIPTION

The following description provides specific details for a thorough understanding and enabling description of these examples. One skilled in the relevant art will understand, however, that the techniques discussed herein may be practiced without many of these details. Likewise, one skilled in the relevant art will also understand that the technology can include many other features not described in detail herein. Additionally, some well-known structures or functions may not be shown or described in detail below so as to avoid unnecessarily obscuring the relevant description.

The terminology used below is to be interpreted in its broadest reasonable manner, even though it is being used in conjunction with a detailed description of some specific examples of the embodiments. Indeed, some terms may even be emphasized below; however, any terminology intended to be interpreted in any restricted manner will be overtly and specifically defined as such in this section.

Various embodiments of the present technology generally relate to surgical tables and accessories. More specifically, some embodiments generally relate to surgical tables and accessories to facilitate hip arthroscopy. Traditional techniques for performing distraction of the hip joint during arthroscopy, or while performing reduction of hip fractures; utilize a perineal post against which the pressure to distract the femur from the acetabulum, or realign the fractured fragments, is transferred, This pressure can, in some instances, fail to sufficiently protect tissues, nerves, blood vessels and other anatomical structures in the groin. As discussed below, various embodiments of a surgical table system in accordance with the present disclosure provide new devices and methods for performing hip distraction without the use of the perineal post, or with minimized pressure on the perineal post, if used.

In accordance with various embodiments, the distraction system may be attached to a surgical table along with a variety of accessories designed to facilitate hip distraction, hip fracture reduction and fixation, or anterior approach hip replacement procedures, with or without a perineal post. FIG. 1 is an isometric view of a surgical table and accessories in accordance with one or more embodiments of the present technology.

In the embodiment illustrated in FIG. 1, a distraction system 1 is attached to a surgical table 2. In some embodiments, the distraction system 1 can include beams or arms 3 connected to base 4 via adjustable joints 5. The beams 3 and base 4 can be secured to surgical table 2 with adjustable locking mechanisms 6 to allow the distraction system 1 to modularly attach to a variety of surgical tables 2, including retrofit of distraction system 1 to pre-existing surgical tables. For example, in the illustrated embodiment, the table 2 includes a table portion sized and configured to receive and support a patient and a pedestal foot sized to provide a stable support for the table portion. In other embodiments, base 4 may be integrally and/or monolithically formed as a part of the pedestal foot of table 2, obviating the need for a separate locking mechanism 6.

In some embodiments, the table 2 is configured to allow the table portion to tilt relative to the pedestal foot, such that the plane of the patient support surface forms angle $\theta$ (FIG. 14) with respect the pedestal foot (and the floor of the room in which system 1 is installed). Angle A, shown in FIG. 1 as the angle between the patient support surface and the vertical axis of the stanchion linking the table portion with the pedestal foot, is complementary to angle $\theta$ (i.e., $\theta=90-A$). Such tilting of the table portion may be used to position the head of the patient below the hip of the patient, e.g., in the Trendelenburg position, as further described below. For purposes of the present discussion, a positive value of angle $\theta$ corresponds to a Trendelenburg tilt in which the patient's head is lower than the patient's hip.

The beams 3 may be solid or hollow in various embodiments. The beams 3 may include one or more rounded transition points in some embodiments. In accordance with some embodiments, these components of distraction system 1 can be made of various materials (e.g., aluminum, carbon fiber, etc.) to provide a balance between strength and light weight for moving.

Locking mechanisms 6 may be removable from base 4 to allow different locking mechanisms to be selected (e.g., to ensure compatibility between the configuration or model of surgical table 2 and the configuration of distraction system 1). In some embodiments, locking mechanisms 6 may include a bracket with an open end that allows the locking mechanisms 6 to wrap around a portion (e.g., a foot or post) underneath the surgical table when slid along the elongated openings 4.5 in base 4. Other types of locking mechanisms may be used as long as the base 4 is securely attached to the surgical table 2 to prevent sliding or twisting.

The distraction system 1 can have a variety of adjustable parts (e.g., adjustable joints 5 and adjustable posts 8) to accommodate patients with a variety of heights from short to tall. Adjustable joints 5 allow the beams 3 to be rotated about pivot shafts 5.5 (which define a generally vertical pivot axis) into a desired medial/lateral position. For example, the beams 3 may be positioned far enough apart to allow for various medical equipment (e.g., imaging equipment) to be positioned between the beams 3. In addition, adjustable joints 5 and adjustable posts 8 can enable disassembly of the unit for transport or storage.

Support posts or stanchions 8 can include locking casters 9 to allow for angular adjustment (e.g., hip adduction and abduction). In accordance with some embodiments, locking casters 9 may be replaced (or supplemented) with other support mechanisms to prevent movement and lateral translation of the support posts 8. Examples of other support mechanisms include, but are not limited to extendable tri-pod like stands and extendable supports.

Support posts or stanchions 8 can include a gear box 10 to allow for vertical adjustment of equipment. Other embodiments may use a simple slide/clamp mechanism instead of the gear box 10. Locking linear slides 7 may be used in some embodiments to couple the beams 3 to the posts 8. The locking linear slide 7 may be used to pull a boot, foot support or other distal patient restraint away from surgical table 2 to apply gross traction for distraction of the femur. In some embodiments, other suitable linear adjusters may be used. For example, linear adjustment mechanisms for applying traction may be used as described herein, including telescoping linear slides.

An upper support post with a mount 11 having standard surgical table rail dimensions allows for attachment of any standard surgical table equipment (e.g., hip positioning systems such as padded boots, foot supports or other distal patient restraints). Additionally, a generic mount 12 may be present at the upper end of the support post for fixation of other equipment either custom or generic. Moreover, any support post arrangement, with a separately affixed or integral/monolithic patient restraint may be used in the present technology. As described herein, support posts may extend upwardly from linear slide 7 (or other linear actuators as described herein), as well as downwardly therefrom in a variety of potential configurations.

Figure 14:
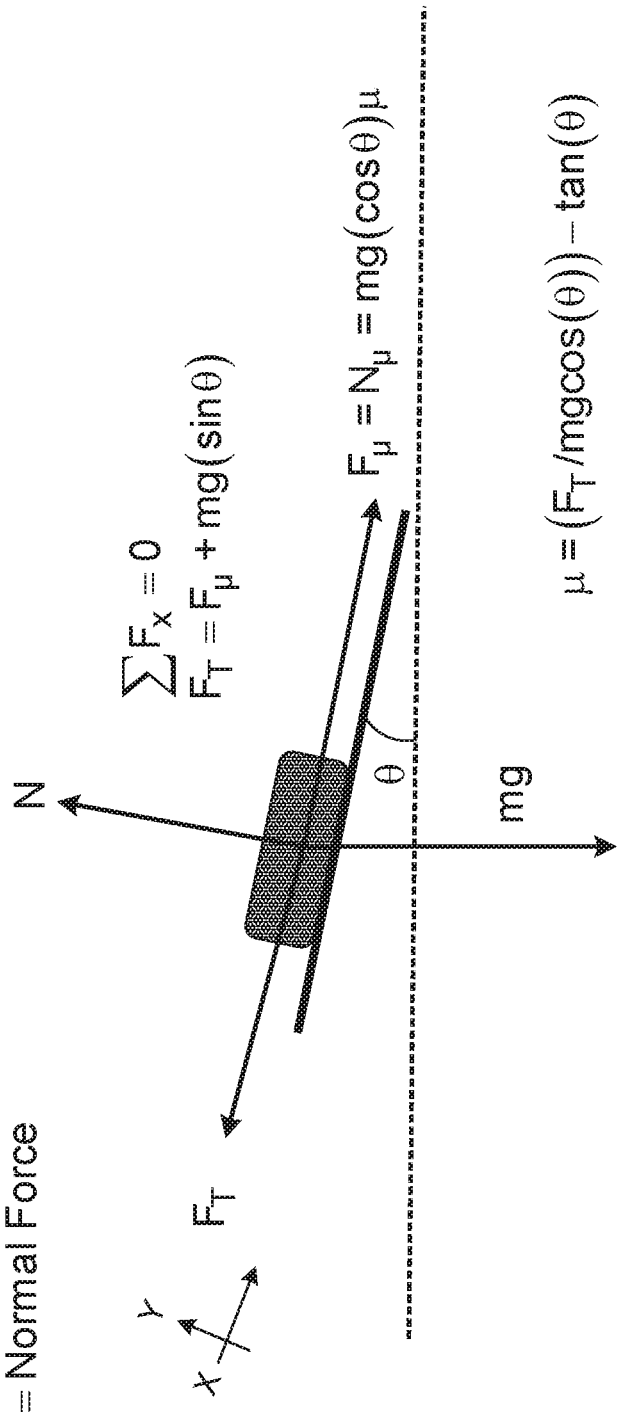
FIG. 14 is a schematic representation illustrating how various friction calculations can be made when a patient is in a declined position on a surgical table with the distraction system that can be used in one or more embodiments of the present technology.

Some embodiments of the present technology include table extension 13 that allows for positioning of the patient on the distal end of the surgical table 2. In some embodiments, the table extension 13 is radiolucent to allow for radiographic imaging of the patient through the table extension. An optional perineal post 14 may be provided and designed to accommodate positioning for either right or left side procedures. In some embodiments, the distraction system does not include a perineal post. Instead, the traction force is provided by a friction pad 15 and/or the tilt angle θ of the table 2, as seen in FIG. 14 and explained more fully below.

Figure 2:
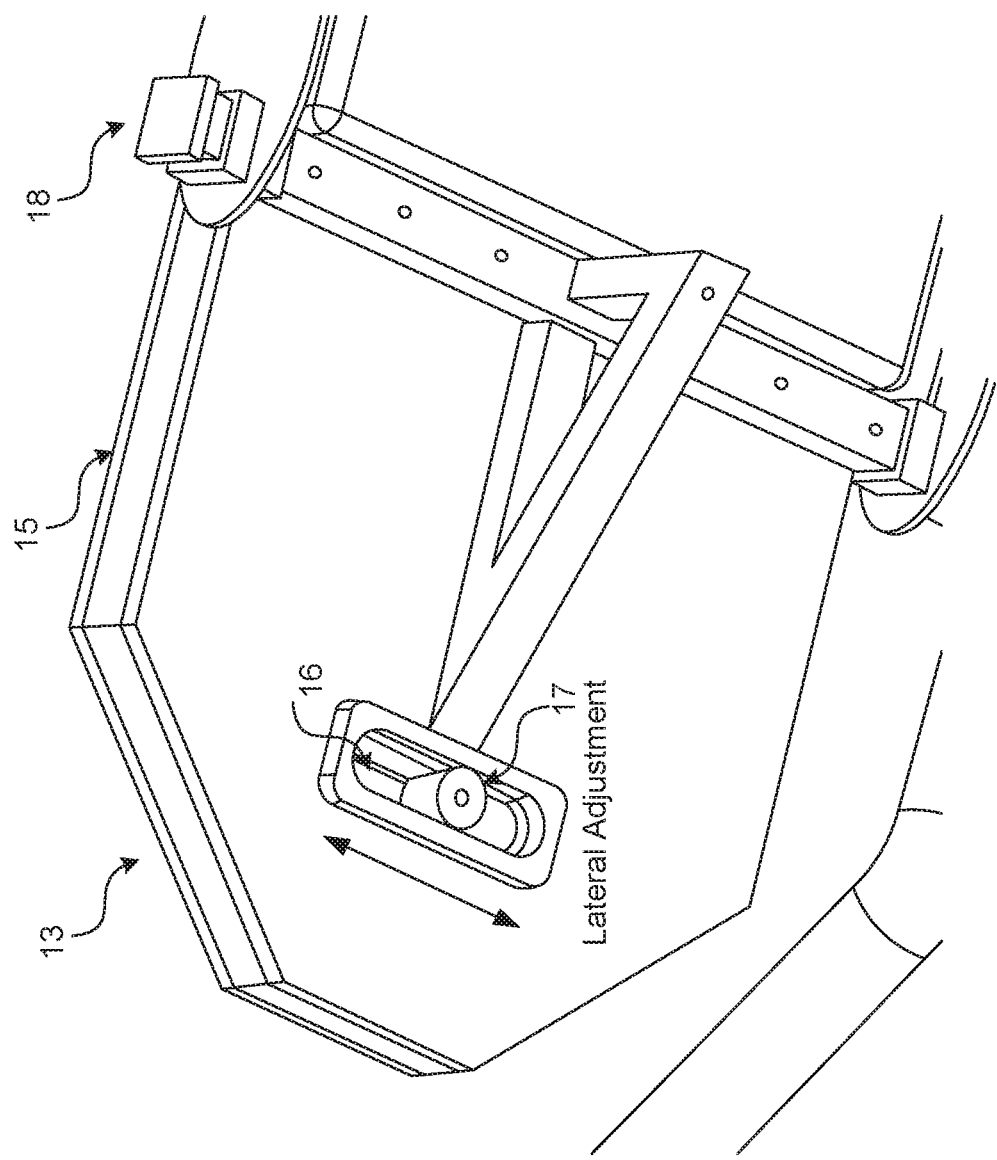
FIG. 2 is an isometric view of a table extension as viewed from underneath that can be used in some embodiments of the present technology.

With reference to FIG. 2, the table extension 13 may be provided in different sizes that can be selected based on the size of the patient, with larger sizes used for larger patients in order to provide for a larger support surface area and greater frictional interaction between the patient and the support surface of extension 13. Also, some embodiments of the table extension 13 can include an elongated aperture 16 in which a supporting extension 17 of the perineal post 14 can be optionally attached as desired by a surgeon. The elongated aperture 16 allows the perineal post to be laterally positioned depending upon the operating leg of the patient. Other embodiments (not shown), may include two or more apertures which provide a series of fixed positions for the optional perineal post. Still yet, some embodiments of table extension 13 may not allow for a perineal post to be attached, or may not have a perineal post installed in aperture 16. The table extension 13 can include an adjustable attachment mechanism 18 that can be used to secure the table extension 13 to surgical tables of different widths (e.g., nineteen inches, twenty inches, etc.). In the illustrated embodiment, attachment mechanism 18 includes a pair of attachment arms engaged (e.g., frictionally) with the lateral surfaces of the table portion of surgical table 2 (as shown in FIG. 1) in order to fix table extension 13 to the distal end of the adjacent patient support surface. Of course, it is contemplated that any suitable attachment mechanism 18 may be used for such fixation, including fasteners, adhesives, or the like. In some embodiments, table extension 13 may be integrally and/or monolithically formed as a part of the table portion of surgical table 2, obviating the need for a separate attachment mechanism 18.

A friction pad 15 can be mounted to an upper surface of extension 13, and can be used in conjunction with the weight of the supported patient to generate forces opposing the distraction force. In combination with the tilt angle θ (e.g., Trendelenburg tilt) of the table, the frictional forces created by friction pad 15 may negate or minimize the need for a counter-traction perineal post. In some embodiments, the addition of a side-tilt of less than 2 degrees (e.g., 0.5 to 2.0 degrees) on the contra-lateral side can further reduce the need for a counter-traction perineal post. The pad may be sized to contact only a portion of the supported patient's body (e.g., lower back, buttocks) to generate lower levels of opposing force as required or desired for a particular application. Alternatively, the pad may extend the entire length of the supported patient's torso to generate increased levels of opposing force as may be required or desired for other applications.

Figure 3:
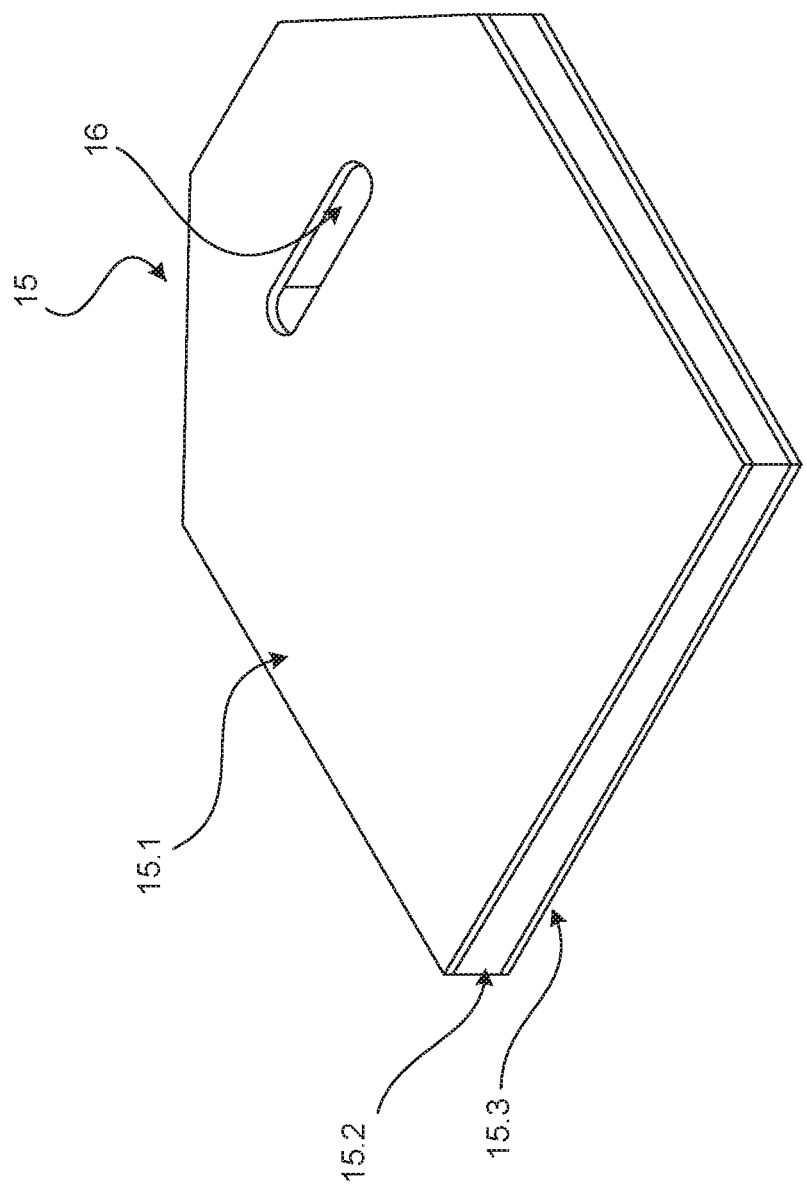
FIG. 3 is an isometric view of a friction pad that can be used in one or more embodiments of the present technology.

FIG. 3 illustrates an exemplary friction pad 15 which can be used in one or more embodiments of the present technology. In accordance with various embodiments, the friction pad 15 may fit over table extension 13. Friction pad 15 may include a composite polymeric patient-contacting pad layer 15.1 that can be used to generate a coefficient of friction ≥0.52 as measured between human skin and the surface of the pad 15.1. For example, friction pad 15.1 may be a polymer-polymer or polymer-textile composite in various embodiments.

Additionally, an additional polymeric table-contacting layer 15.3 may be used in some embodiments to generate a coefficient of friction ≥0.52 as measured between the pad and the abutting surface of the surgical table 2. The middle layer 15.2 of the pad 15 can be designed to provide cushioning and support for the patient and to create a level surface between the surgical table 2 and the extension 13. The friction pad 15 may be a disposable pad which can be thrown away at the end of each use. In some embodiments, the friction pad 15 may be a disposable, sheet like covering for reusable surgical table cushions.

Figure 4A:
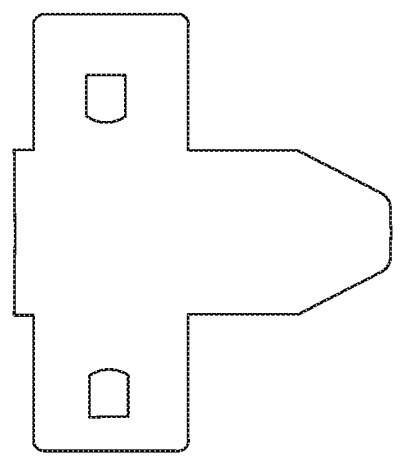
FIGS. 4A and 4B are top views of other friction pads that can be used in various embodiments of the present technology.
Figure 4B:
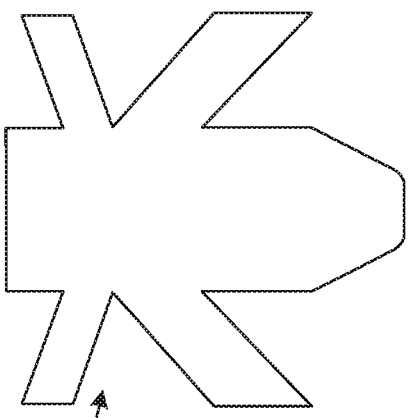

FIGS. 4A and 4B are top views of other friction pads 15 that can be used in various embodiments of the present technology. In addition to the functions previously described for the friction pad 15, these embodiments of the friction pad 15 are designed to extend past the table extension 13 and cover all or part of the length of the surgical table 2 and provide restraint for the patient's arms during the procedure. The additional wrapping portions of the friction pads 15 that are used to assist in restraining the patient may include one or more apertures allowing access for fluid delivery or the like. As a result, one side of the friction pad 15 may generate friction as the patient is positioned thereupon and the access material can be positioned (e.g., wrapped) around the patient to secure his hands or arms. The patterned material for wrapping and securing the arms of the patient may be the same or different material found on the rest of the friction pad (e.g., the portion that would be underneath the patient's back). In addition, friction pads 15 may be made of a flame resistant or flame retardant material.

Figure 5:
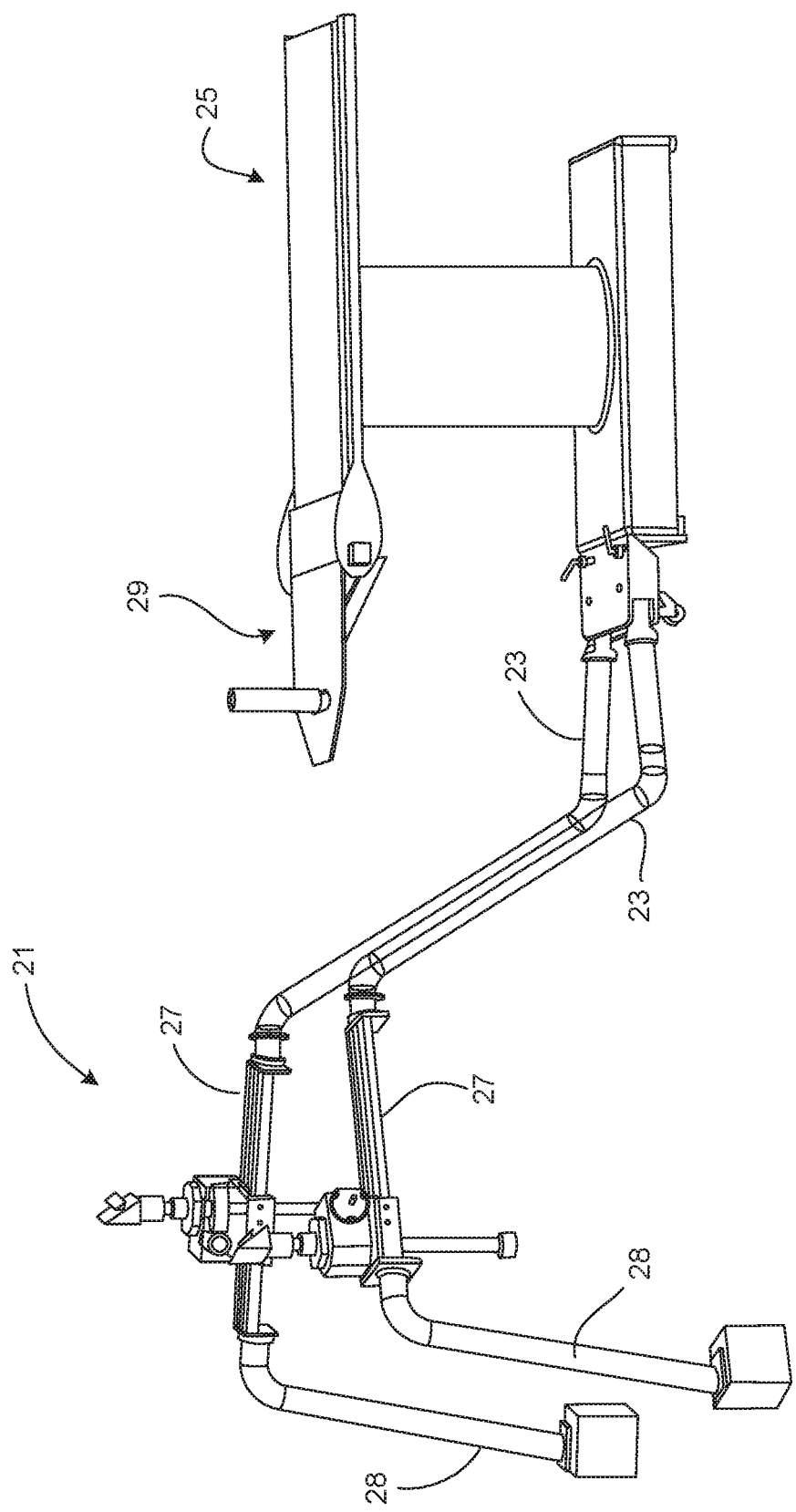
FIG. 5 is a perspective view of a surgical table and distraction system according to some embodiments of the present technology.

FIG. 5 is a perspective view of a surgical table 25 and distraction system 21 according to another representative embodiment of the present technology. Table 25 and distraction system 21 may be similarly constructed to table 2 and distraction system 1 described in detail above, with like structures having like functions except as otherwise described below.

In the embodiment shown in FIG. 5, the support posts 28 have been relocated from the embodiment shown in FIG. 1, to decouple the angular positioning (adduction and abduction) from the gross traction mechanism 27. Thus, in the embodiment of FIG. 5, gross traction mechanism 27 (which operates similar to locking linear slide 7 described above) may be actuated without moving support posts 28. Support posts 28 may include fixed footers at their ground-contacting surfaces, rather than locking casters 9, of distraction system 1 (FIG. 1), since posts 28 need not translate during distraction. Alternatively, locking casters 9 may be provided on posts 28 to facilitate medial/lateral pivoting of beam members 23.

Figure 11:
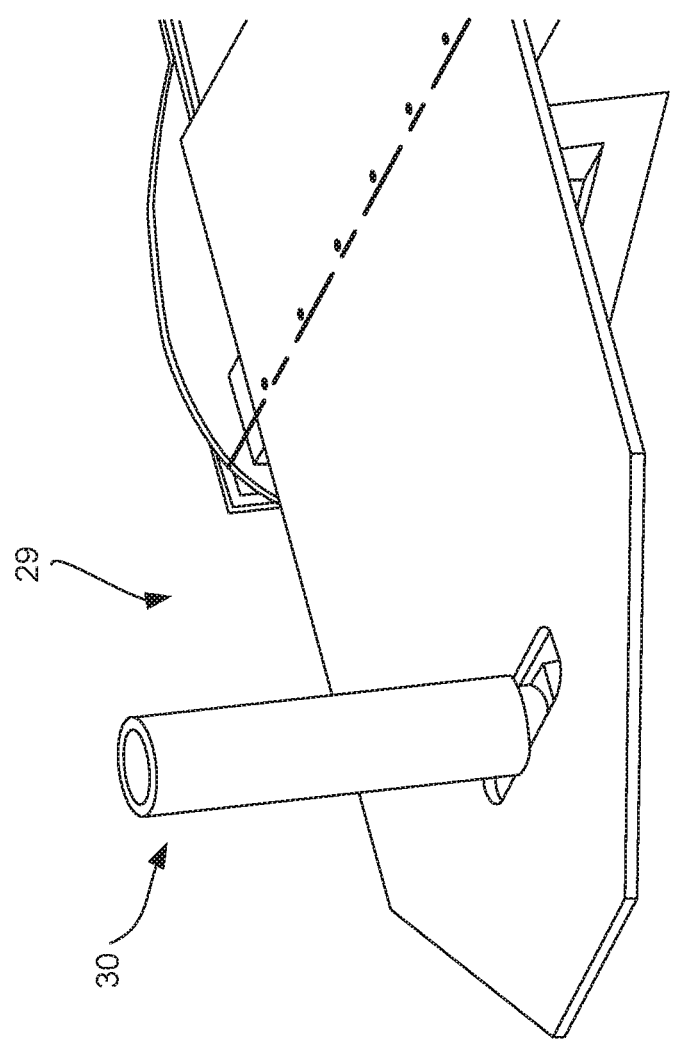
FIG. 11 is a partial perspective view of a friction pad with a removable perineal post that can be used in one or more embodiments of the present technology.

FIG. 11 is an enlarged, partial perspective view of the table extension 29 shown in FIG. 5. Table extension 29 allows for positioning of the patient on the distal end of the surgical table 25, similar to table extension 13 described in detail above with respect to surgical table 2. An optional perineal post 30 may be provided and designed to accommodate positioning for either right or left side procedures, similar to perineal post 14 also described in detail above.

Other embodiments of the present technology, while not pictured, can include a linear slide mechanism incorporated into the beam members 23 to minimize weight and size of the invention. In such an embodiment, a D-shaped, dovetail, or double dovetail profile for the beam members 23, with a locking clamp, may be used in place of gross traction mechanism 27 to apply gross traction. Additionally, in some embodiments, a fine traction adjustment mechanism may be added using a linear/rotary motion conversion mechanism, such as a worm gear or a trapezoidal threaded rod (sometimes referred to as an acme rod) and correspondingly threaded rotary bushing. Such a fine adjustment assembly may be used, for example, to allow for a mechanical reduction such that movement of an input (e.g., a hand wheel or motor mandrel) is translated to a corresponding but reduced linear movement of the distal patient support.

Figure 6:
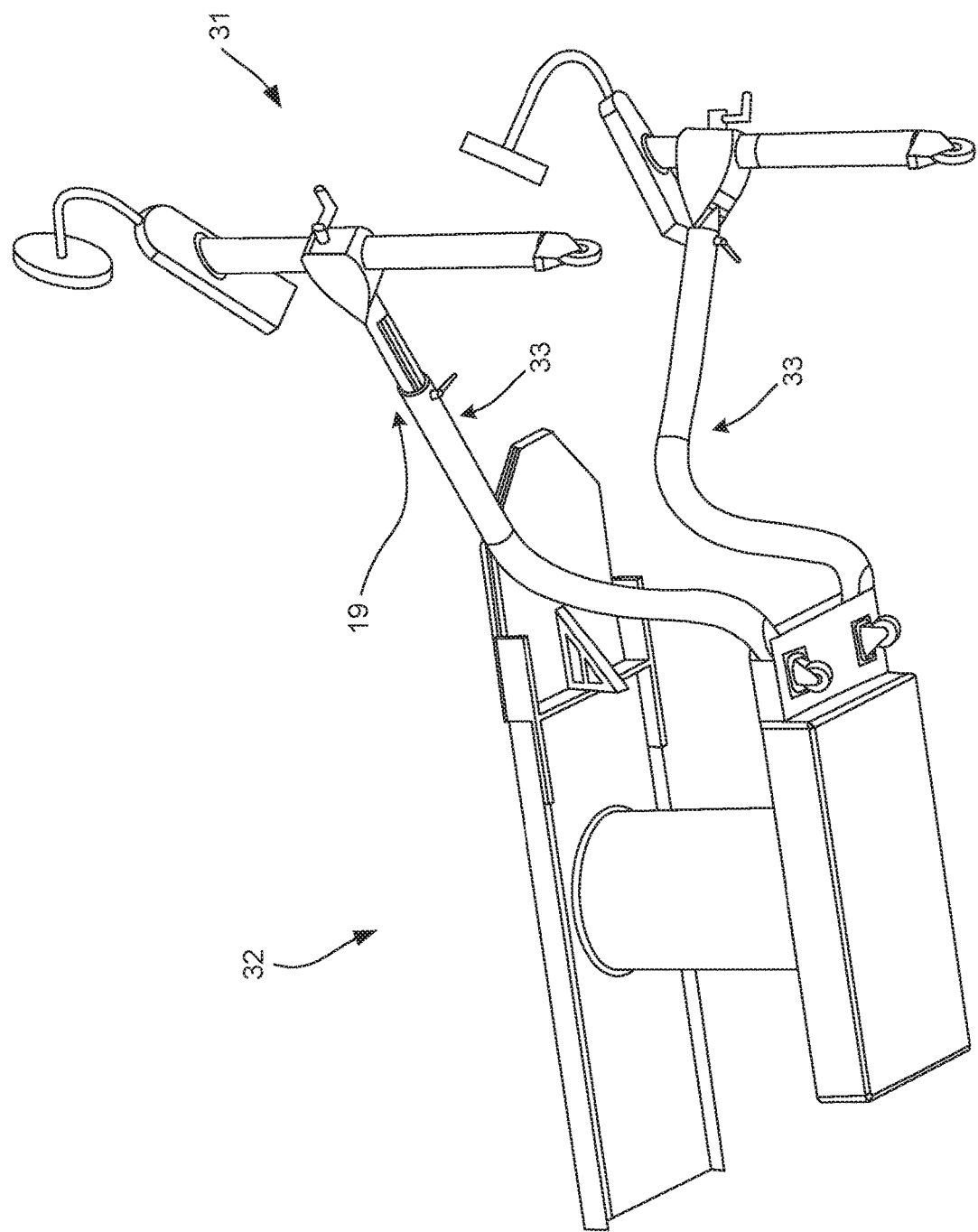
FIG. 6 is an isometric view of a surgical table and distraction system with a telescoping linear slide according to one or more embodiments of the present technology.
Figure 8:
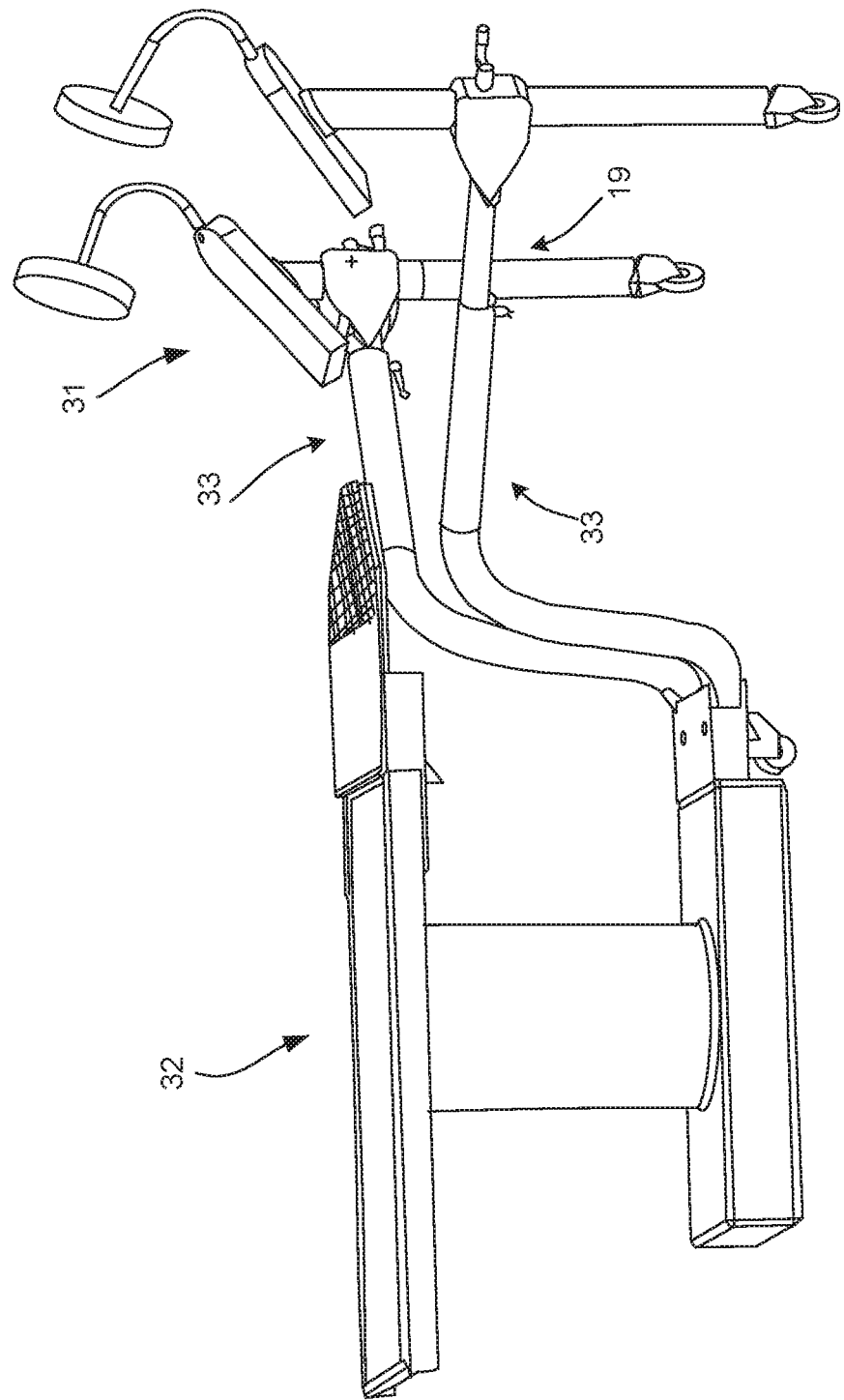
FIG. 8 is a perspective view of a surgical table and distraction system according to some embodiments of the present technology.
Figure 9:
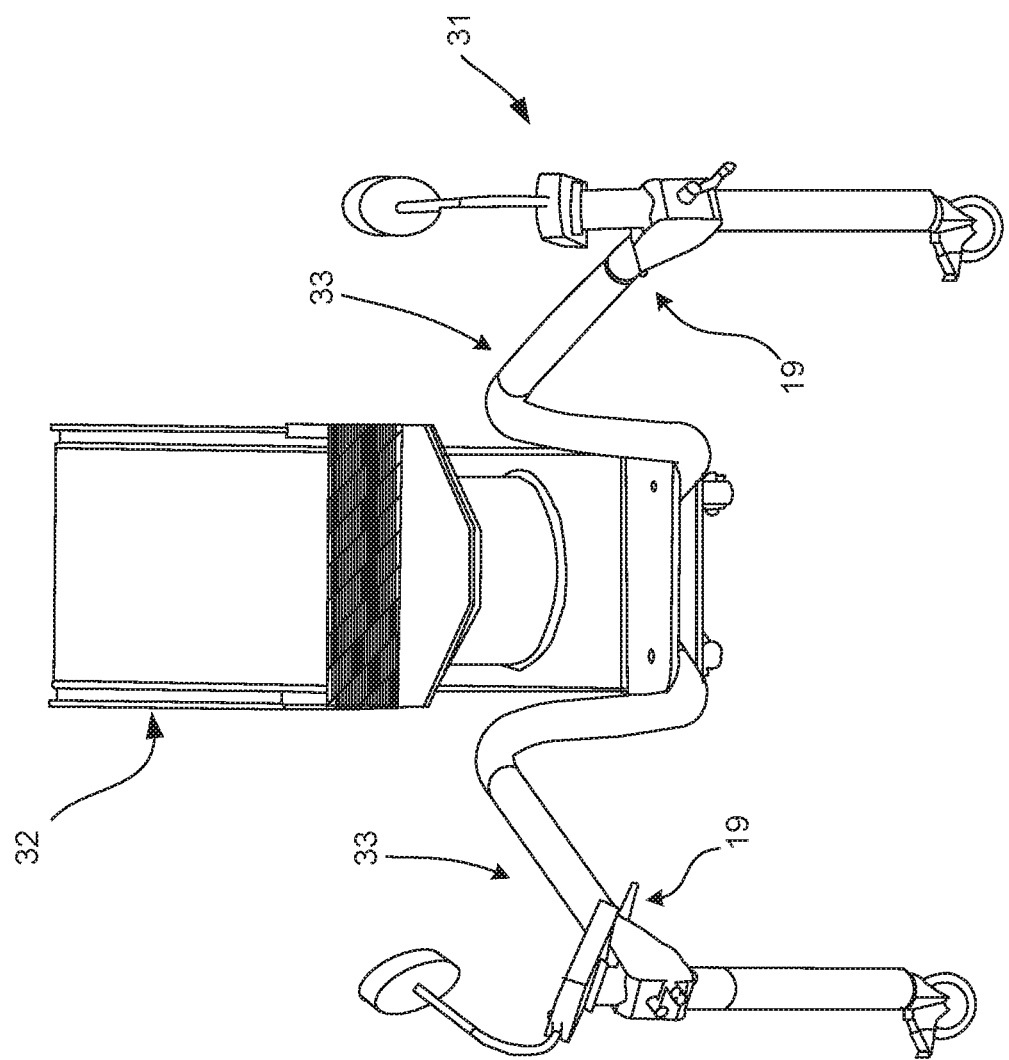
FIG. 9 is a perspective view of a surgical table and distraction system according to one or more embodiments of the present technology.
Figure 10:
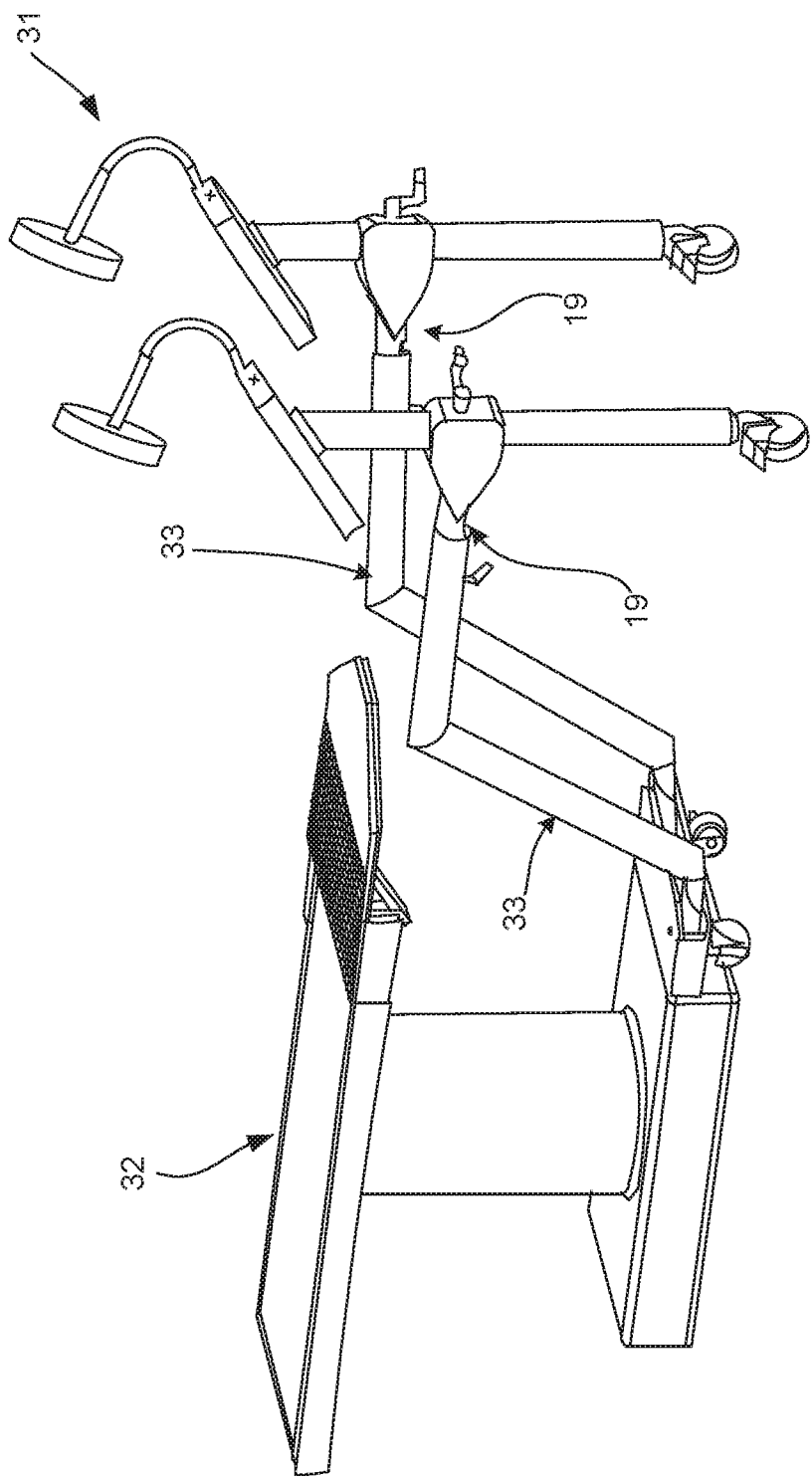
FIG. 10 is an isometric view of a surgical table and distraction system according to various embodiments of the present technology.

FIG. 6 illustrates another conceptual representation of a perspective view of a surgical table 32 and distraction system 31 with a telescoping linear slide 19 on each of the beam members 33 according to one or more embodiments of the present technology. FIGS. 8-10 provide various perspective views of the surgical table 32 and the distraction system 31 introduced in FIG. 6.

FIGS. 7A-7C are enlarged cross-sections of various linear slides mentioned above that may be used in various embodiments of the present technology. For example, FIG. 7A illustrates a D-shaped slide profile 35; FIG. 7B illustrates a dovetail slide profile 37; and FIG. 7C illustrates a double dovetail slide profile 39. In some embodiments, an additional wheel type handle may be present in some embodiments to allow for fine traction adjustment, such as by linear/rotary motion conversion mechanism as discussed above. Other embodiments may include sliding features that may be electro-mechanically, pneumatically, or hydraulically adjustable (e.g., either actively or passively). Some embodiments may use a combination of sliding and controlled linear/rotary (e.g., acme rod) adjustment along beam members 33 to facilitate gross traction in patient on surgical table 32.

Figure 12:
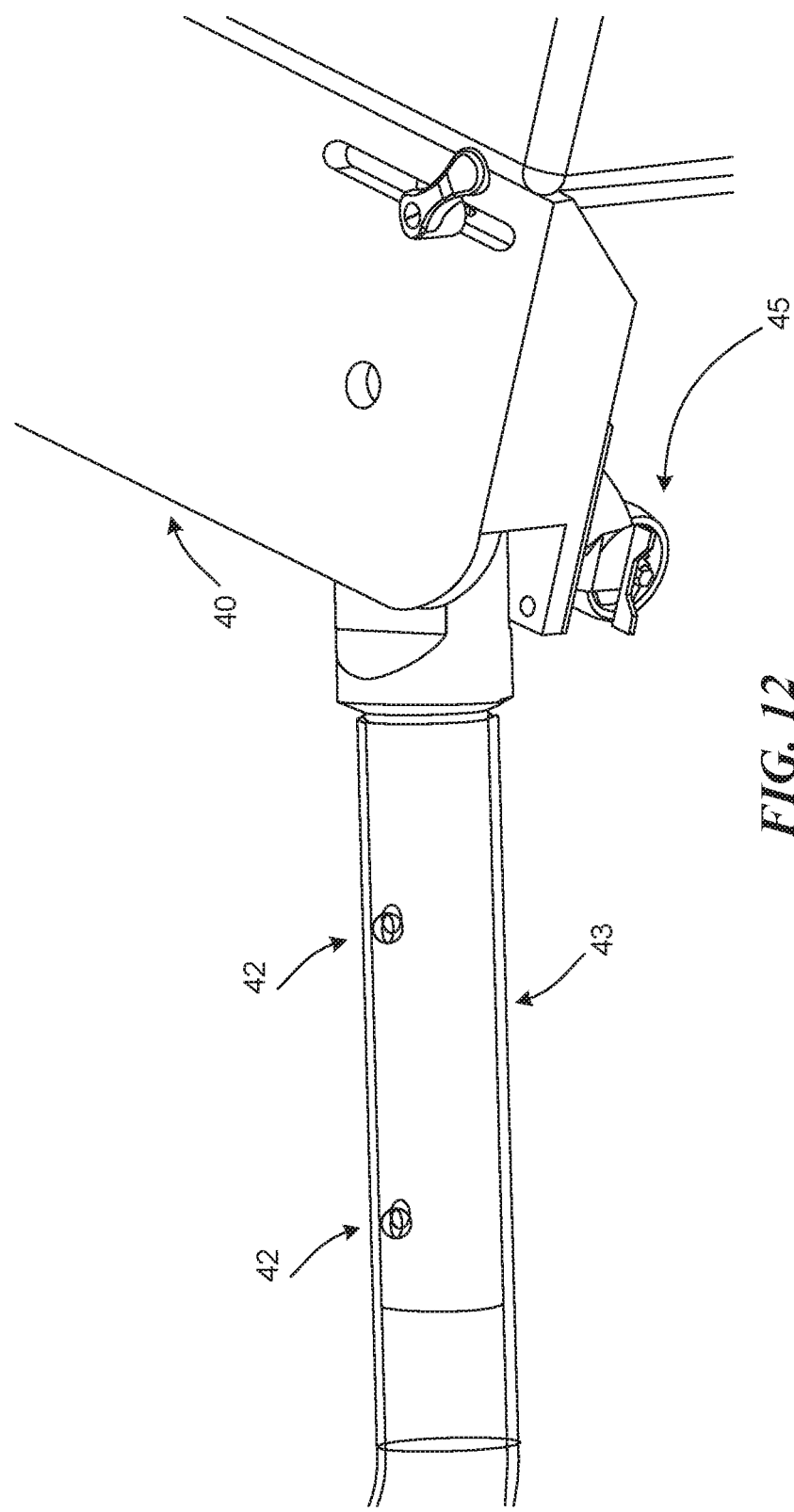
FIG. 12 is an enlarged partial perspective view of portion of a base platform that can be used in accordance with some embodiments of the present technology.

FIG. 12 is an enlarged partial view of a representative embodiment of a base platform 40 that can be used in accordance with some embodiments of the present technology. The beam 43 may allow for length adjustments near base platform 40 using a pin system (e.g., clevis pins) 42 that join nested or telescoping tubing segments in various discrete length-adjustment configurations. The base platform 40 may also include locking/leveling casters 45 for support and adjustment of base platform 40 relative to, or in conjunction with, the surgical table (e.g., surgical table 2 shown in FIG. 1).

Figure 13:
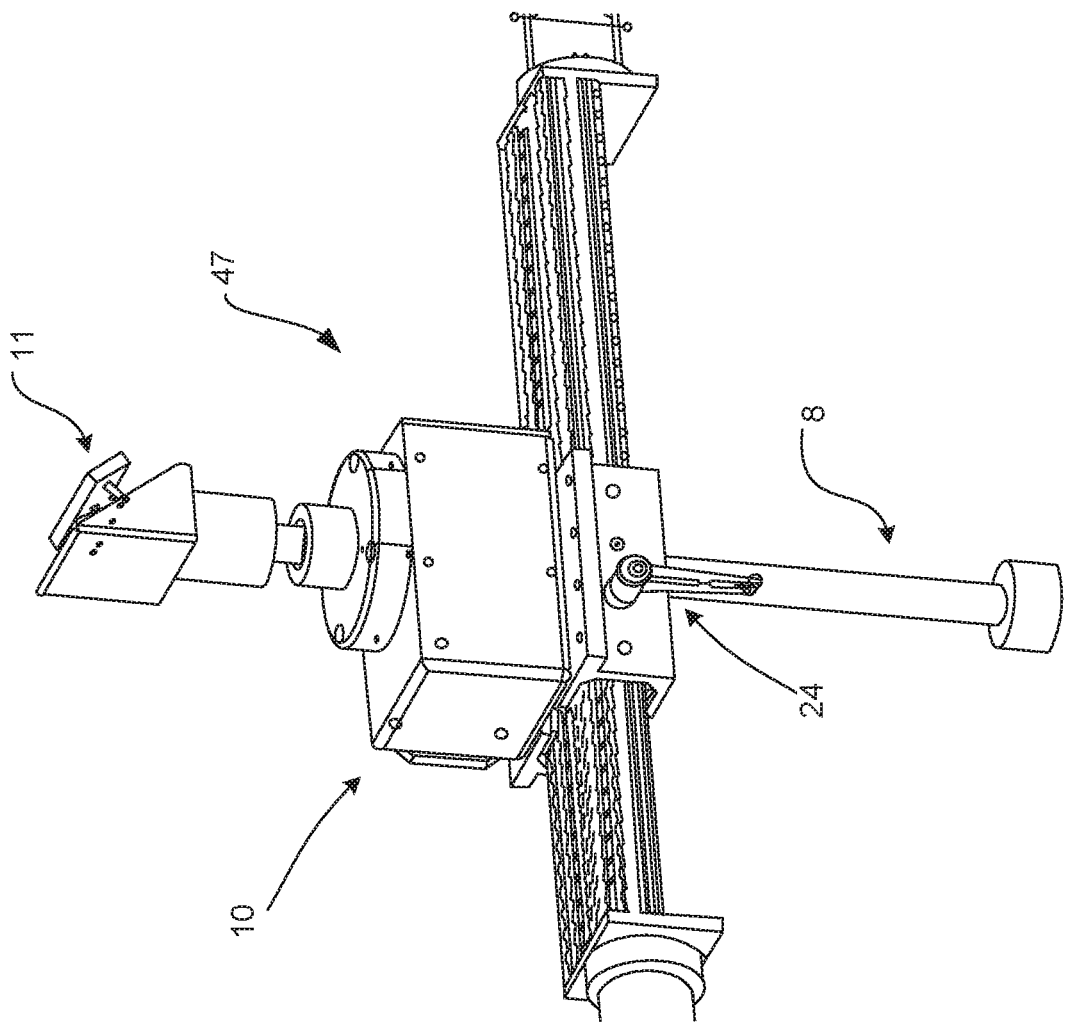
FIG. 13 is an enlarged partial perspective view of a sliding mechanism that can be used in various embodiments of the present technology.

FIG. 13 is an enlarged partial perspective view of a sliding mechanism 47 that can be used in various embodiments of the present technology. The sliding mechanism can provide linear gross traction and/or fine traction and can be used in conjunction with any of the distraction system described herein to provide for linear movement. Similar to locking linear slides 7 described above with respect to FIG. 1, sliding mechanism 47 may be actuated to move mount 12 (and/or any attached or other distal patient restraint) towards or away from the surgical table to reduce or increase traction, respectively. Sliding mechanism 47 can be locked in position with locking clamp 24. In the illustrated embodiment, support posts or stanchions 8 in conjunction with gearbox 10 allow for vertical adjustment of equipmentthough other arrangements may be used (e.g., the arrangement of FIG. 5).

Figure 15:
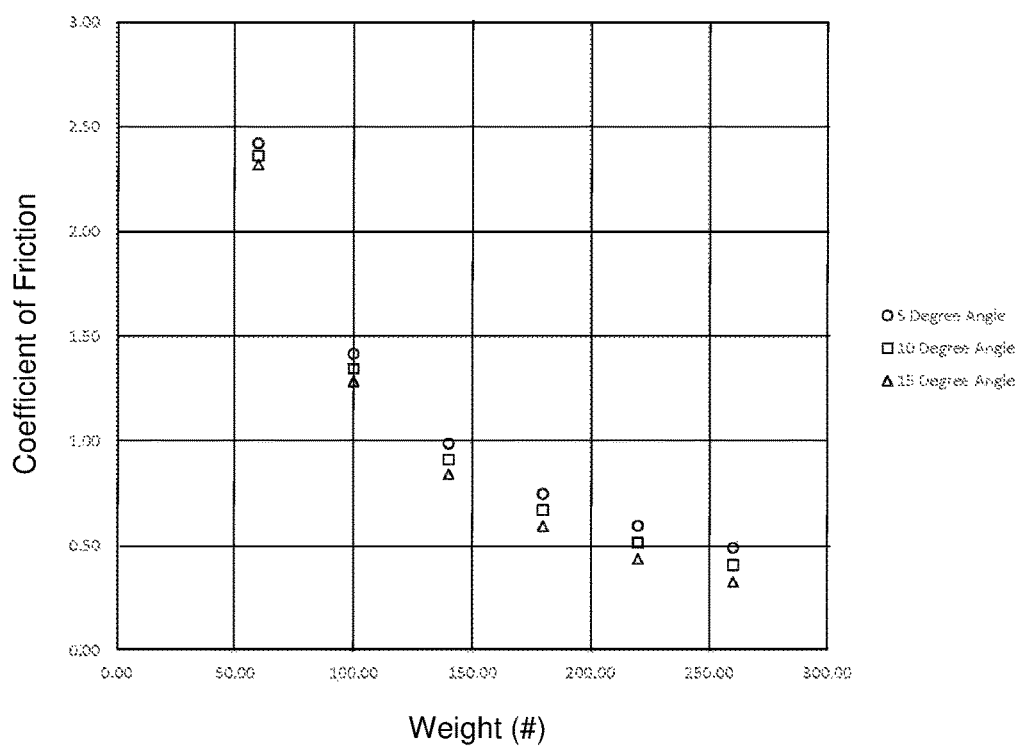
FIG. 15 is a chart illustrating coefficient of friction calculations for various weights.

FIG. 14 is a schematic representation illustrating how various friction calculations can be made when a patient is in a declined position on a surgical table with the distraction system that can be used in one or more embodiments of the present technology. FIG. 15 is a chart illustrating coefficient of friction calculations based on an angle θ for various weights (i.e., the weight of a patient or a portion of a patient received on a patient support surface, as described herein, is the product of the mass m of the patient or portion of the patient and gravity g). The friction pad 15 illustrated in FIG. 1 can be selected to adjust the friction coefficient. As a result, the patient resting upon the patient support surface of surgical table 2 can be placed in a tilted position at a desired angle θ. This combination of tilting and friction generates a force $F_\mu$ which is a function of the Trendelenburg angle θ, the mass m of the patient, and the coefficient of friction μ of the friction pad 15 as detailed in FIG. 14. For a given patient mass m, the Trendelenburg angle θ and the coefficient of friction μ can be selected to provide a desired force $F_\mu$ to sufficiently counteract the required or desired traction force $F_T$, which acts directly opposite force $F_\mu$ as shown. These counteracting forces will keep the patient in place while allowing the surgeon to generate enough traction force $F_T$ on the leg of the patient to gain access to the central hip joint compartment of the patient without the use of a perineal post or to minimize pressure between the patient and a perineal post for configurations including a perineal post is used. In some embodiments, the angle θ can vary in the range from about 0 degrees to about 25 degrees, while the coefficient of friction p may also be varied together with the area of contact between the patient and the friction pad 15 in order to generate the necessary counteracting forces. Various combinations and permutations of these variable factors are illustrated in the tables of FIG. 15 to provide a sampling of potentially viable combinations based on patient weight.

Figure 16:
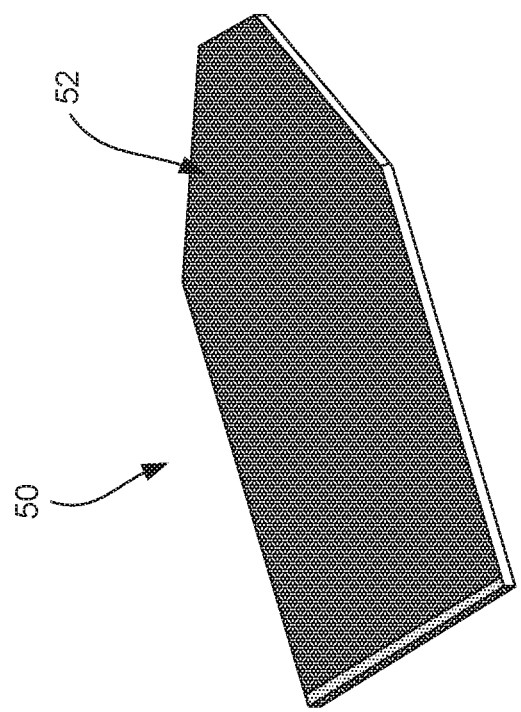
FIG. 16 is an isometric view of a friction pad that can be used in some embodiments of the present technology.

FIG. 16 is an isometric view of a friction pad 50 that can be used in some embodiments of the present technology. The friction pad 50 illustrated in FIG. 16 does not include a cutout for a perineal post, though such a cutout may be provided as described above with respect to friction pad 15.

Figure 17:
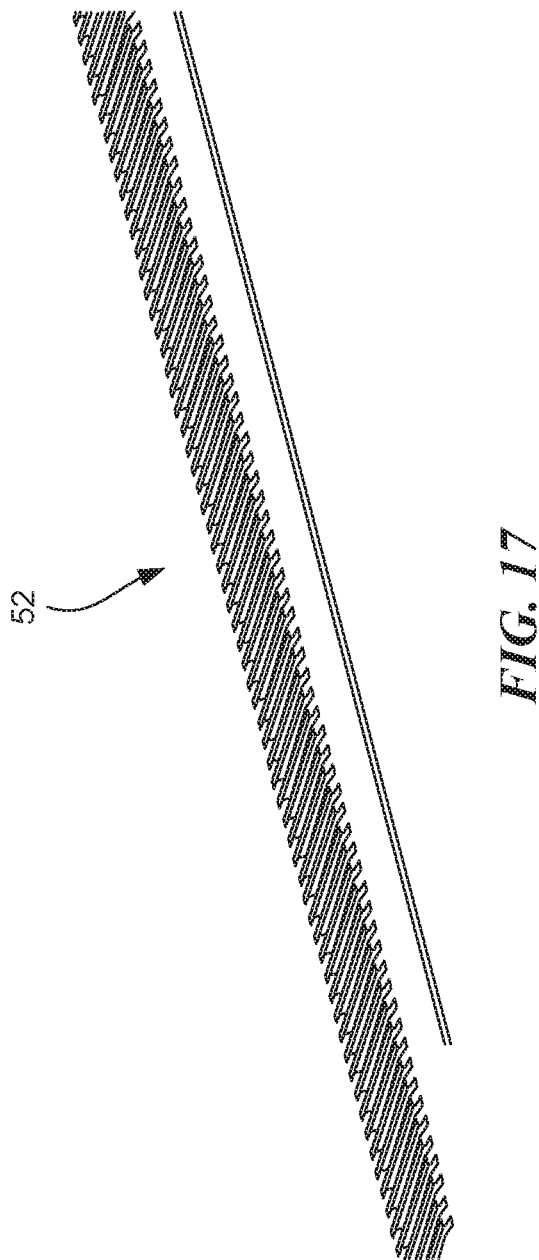
FIG. 17 is a partial perspective view in cross-section of a material that can be used in one or more embodiments of the present technology.

FIG. 17 is a partial perspective view of a friction pad material 52 that can be used in one or more embodiments of the present technology. As illustrated, a series of angled ridges may be provided in the patient-support surface of pad material 52. In one embodiment, these ridges may be oriented to point generally opposite the direction of force $F_\mu$ (FIG. 14) when friction pad 50 is in use, such that a compressive force is placed on the ridges. Each ridge may therefore resiliently deform when the patient is resting on pad 50, presenting a barrier to sliding movement of the patient, upon the patient support surface, effectively increasing the coefficient of friction μ of the pad material 52.

Figure 18:
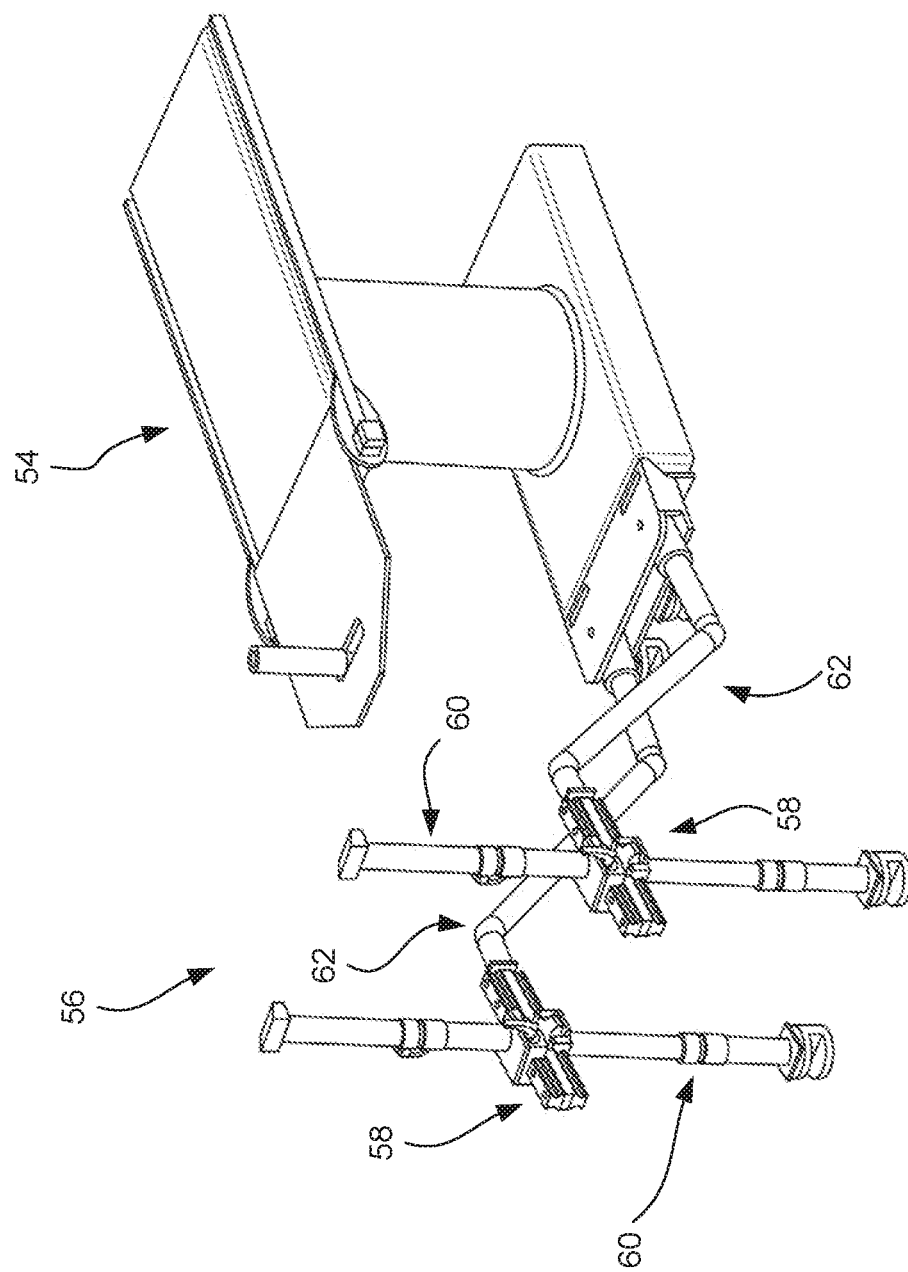
FIG. 18 is an isometric view of a surgical table, distraction system, and accessories in accordance with one or more embodiments of the present technology.

FIG. 18 is an isometric view of a surgical table 54, distraction system 56, and various accessories in accordance with one or more embodiments of the present technology. Distraction system 56 is arranged similar to distraction system 7 shown in FIG. 1 and described in detail above, except that the linear bearings 58 and support posts 60 are differently arranged as described further below.

Figure 19:
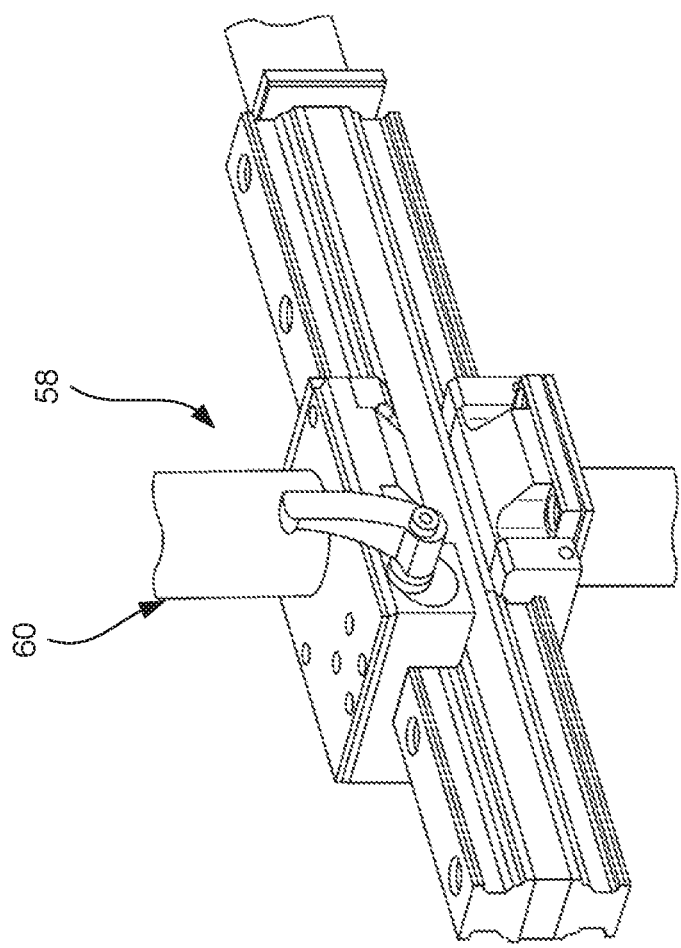
FIG. 19 is an isometric view of a dual linear bearing that can be used in accordance with one or more embodiments of the present technology.

FIG. 19 is an isometric view of the dual linear bearing 58 used in distraction system 56 introduced in FIG. 18. As illustrated, dual linear bearing 58 uses one bearing along the bottom of the linear slide, and a second bearing along the top of the linear slide. The bottom and top bearings may be independently adjustable. The dual linear bearings 58 (slides) illustrated in FIG. 19 can be used in some embodiments to enhance support of the transverse loads on the support posts 60.

Figure 20:
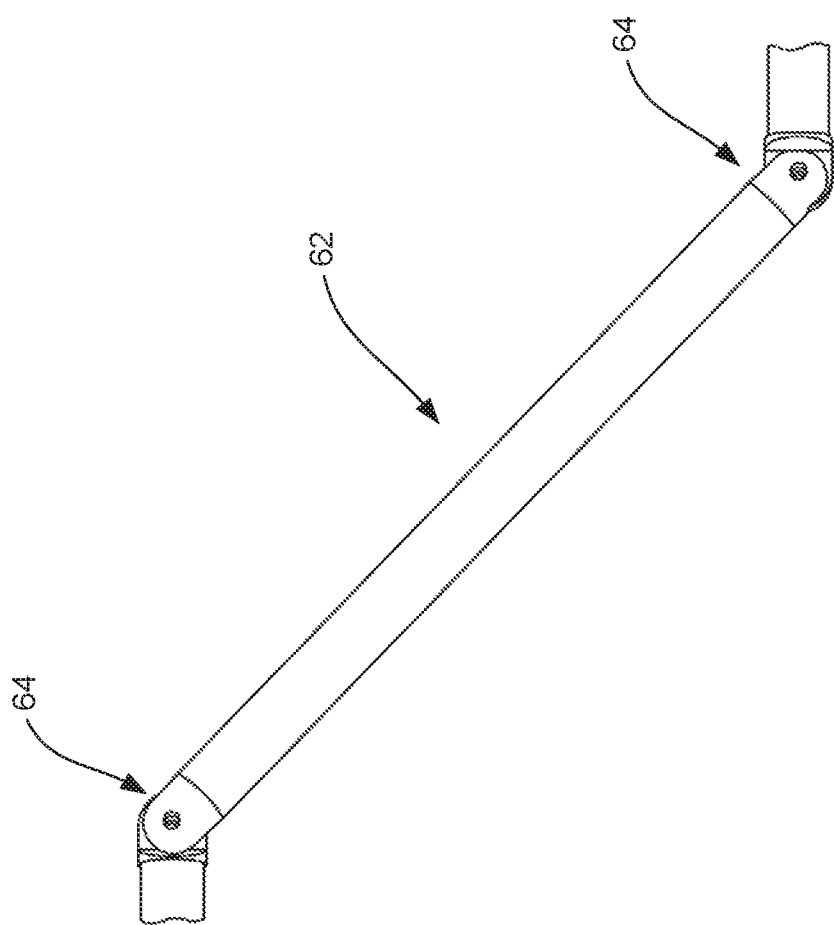
FIG. 20 illustrates hinges in an arm of a distraction system in accordance with one or more embodiments of the present technology.

FIG. 20 illustrates hinges 64 in an arm or beam 62 of a distraction system 56 in accordance with one or more embodiments of the present technology. In the embodiments illustrated in FIG. 20, the arms 62 of the distraction system 56 include hinges 64 to adjust the angle of the arm 62 with respect to the floor. This feature may allow for a better fit of the system to an individual patient.

Figure 21:
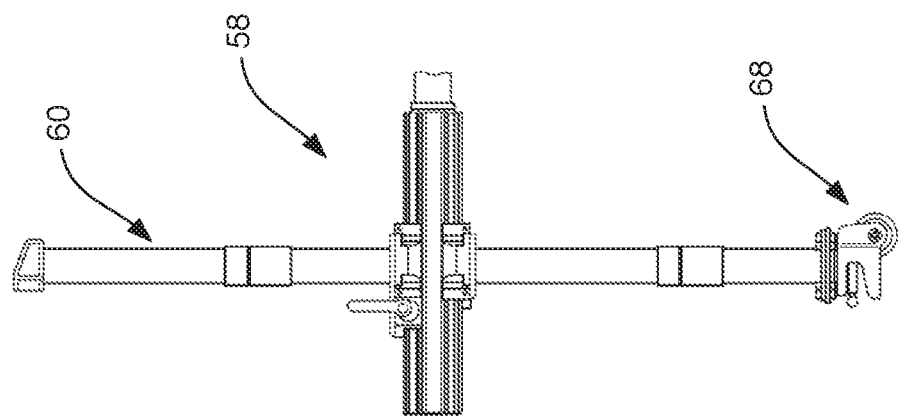
FIG. 21 illustrates a telescoping support post of a distraction system that can be used in accordance with one or more embodiments of the present technology.

FIG. 21 illustrates a telescoping support post 60 of a distraction system 56 that can be used in accordance with one or more embodiments of the present technology. As illustrated in FIG. 21, the support posts 60 above and below the linear bearings 58 (slide) include a telescoping feature which also helps fit the system to an individual patient.

Figure 22:
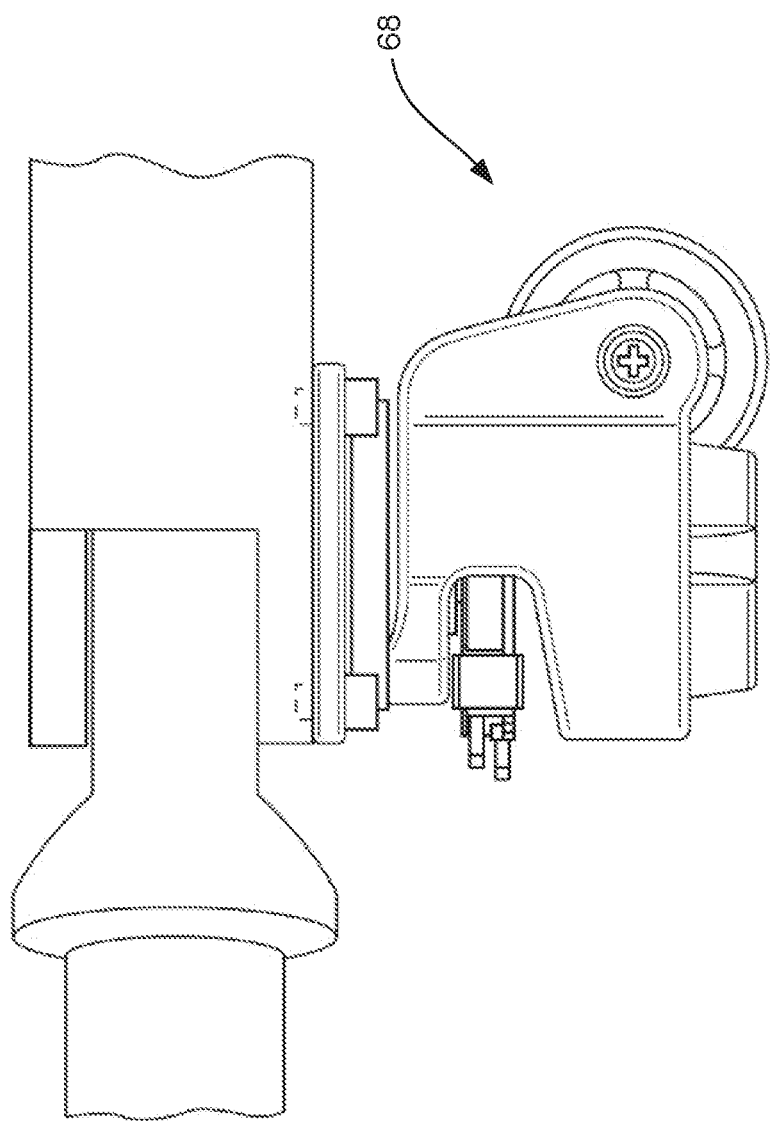
FIG. 22 illustrates a leveling caster of a distraction system in accordance with one or more embodiments of the present technology.

FIG. 22 illustrates a leveling caster 68 of a distraction system 56 in accordance with one or more embodiments of the present technology. The leveling casters 68 can be used to ensure the distraction system 56 maintains equal contact with the floor under all loading scenarios.

Figure 23:
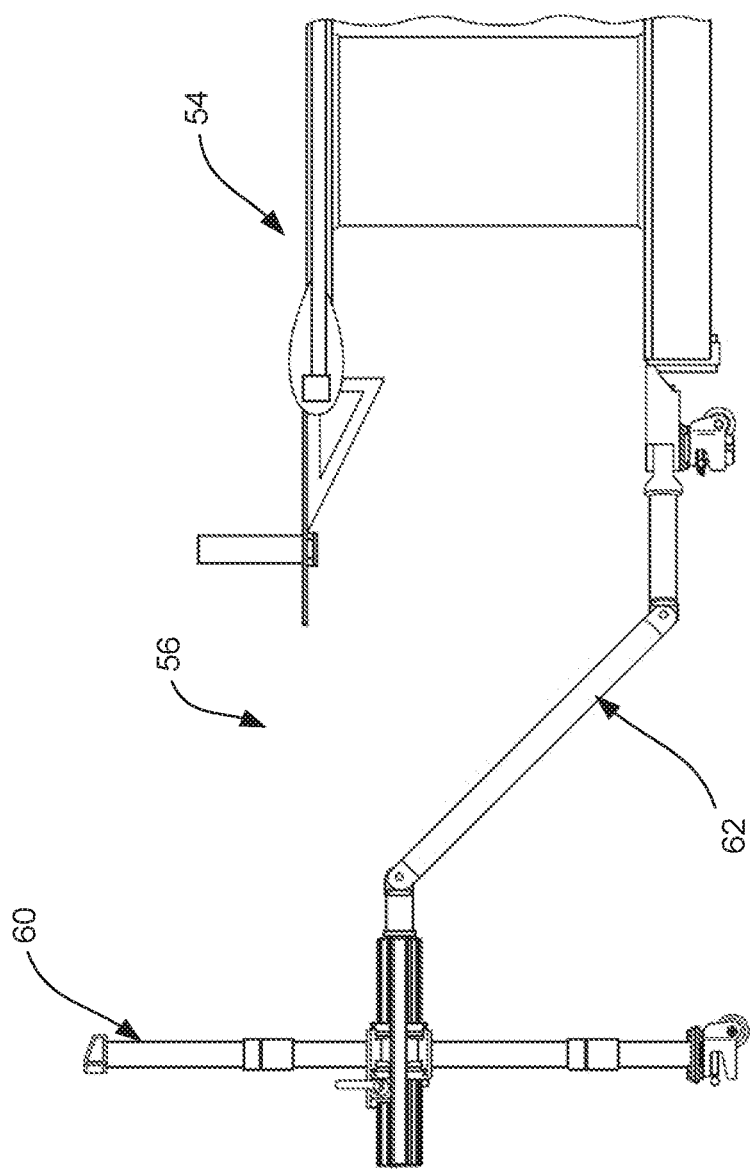
FIG. 23 is a side view of a distraction system with carbon fiber components in accordance with one or more embodiments of the present technology.

FIG. 23 is a side view of a distraction system 56 with carbon fiber components in accordance with one or more embodiments of the present technology. In some embodiments, the beams 62, support posts 60, and/or other components may be made of carbon fiber. Carbon fiber tubing can replace aluminum tubing in order to produce a lighter, stronger, and stiffer distraction system 56.

Figure 24:
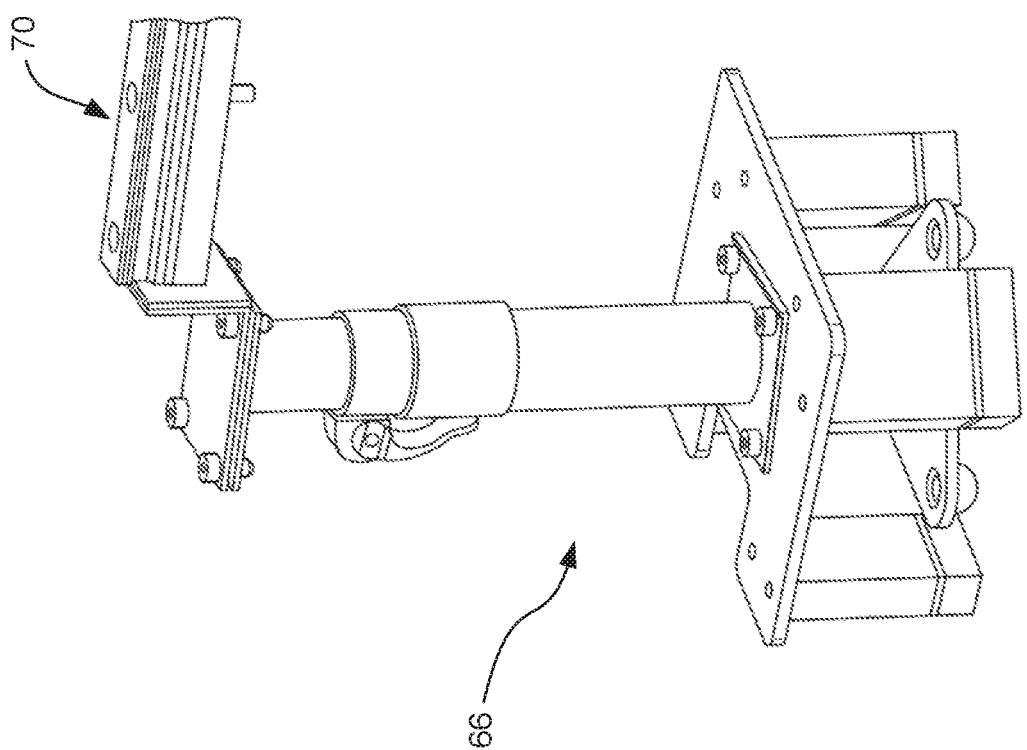
FIG. 24 illustrates an end post design of a distraction system in accordance with one or more embodiments of the present technology.

FIG. 24 illustrates an end post assembly 66 of a distraction system in accordance with another embodiment of the present technology. The support of the linear bearing 70 is shifted to an 'end-post' design in order to allow for a single sliding surface on linear bearing 70 when pulling traction. As illustrated in FIG. 24, the end post design can support the weight of the distraction system independent from sliding surface of bearing 70.

Figure 25:
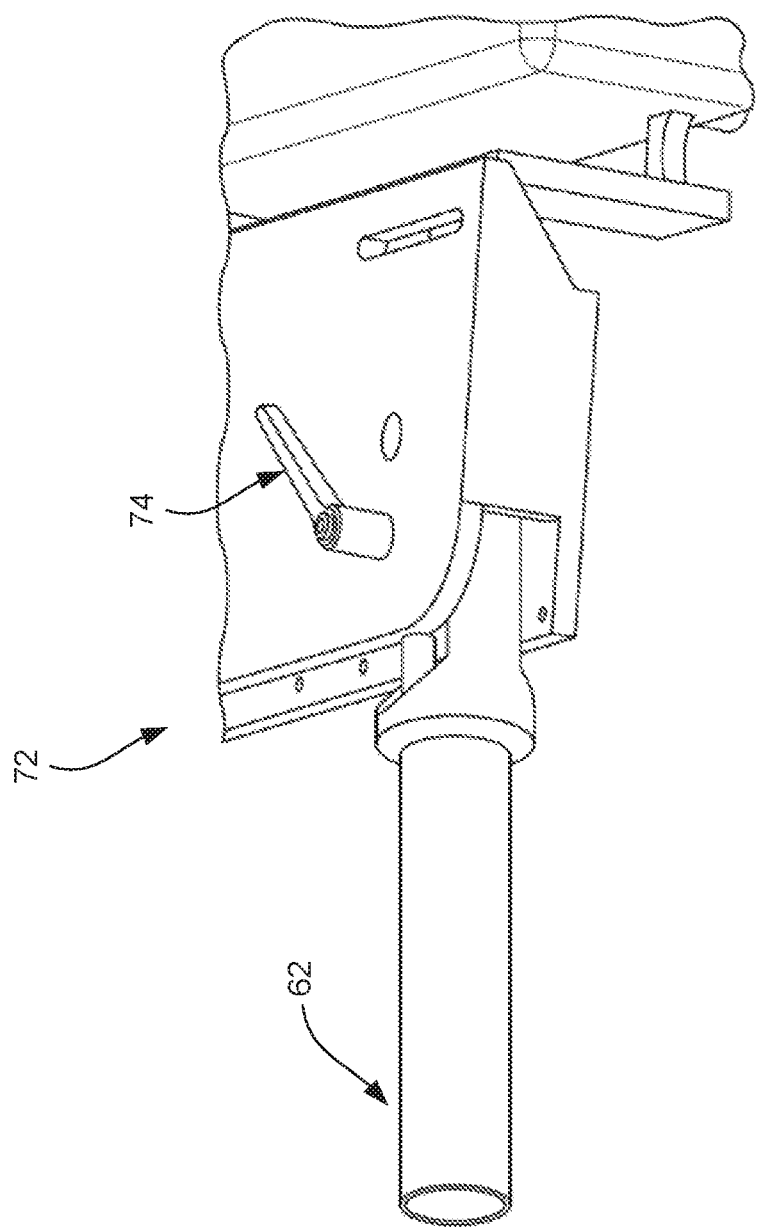
FIG. 25 illustrates a locking stability mechanism of a distraction system that can be used in accordance with one or more embodiments of the present technology.

FIG. 25 illustrates a locking stability mechanism 72 of a distraction system that can be used in accordance with one or more embodiments of the present technology. The handle 74 shown is configured to lock the arm 62 in a desired adduction degree configuration, limiting or eliminating the freedom of arm 62 to move when so locked. This locking can be used to improve stability of the distraction system.

Figure 26:
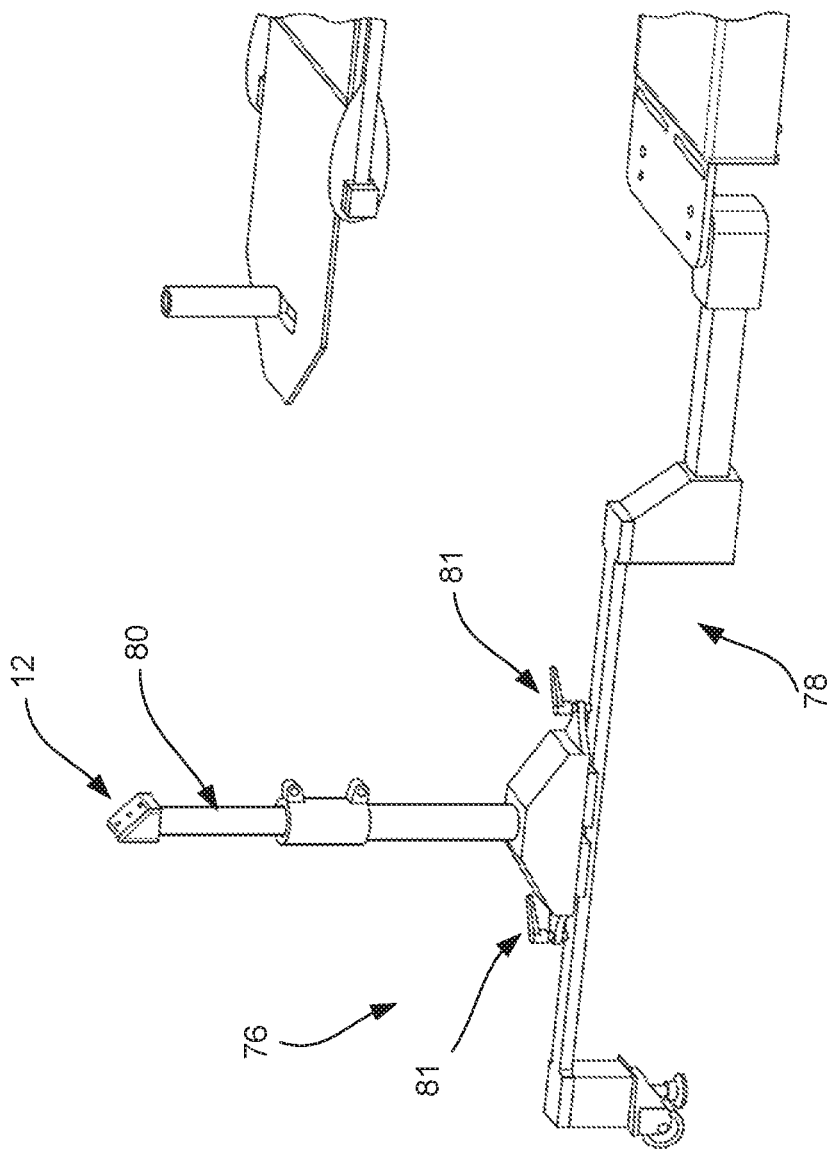
FIG. 26 is an isometric view of an alternate frame design using lower fixed rail and fixed geometry of a distraction system in accordance with one or more embodiments of the present technology.

FIG. 26 is an isometric view of an alternate distraction system 76 using a lower fixed rail 78 and fixed geometry for the distraction system in accordance with one or more embodiments of the present technology. The alternate frame design illustrated in FIG. 26 provides for a lower a rail 78 closer to the ground. In some embodiments, the frame may be made out of machined aluminum. The rail components may be fixed in length and geometry. The post 80 is telescoping in order to adjust the height of mount 12 (and/or any attached or other distal patient restraint). The degrees of abduction may be varied but no locking mechanism is required. Traction may be achieved by sliding the post 80 along the rail 78, and may be locked in place by actuation of locking handles 81. Distraction system 76 is shown attached to a surgical table, and may be used in conjunction with any suitable surgical table as described herein with respect to other embodiments of the present technology.

Figure 27:
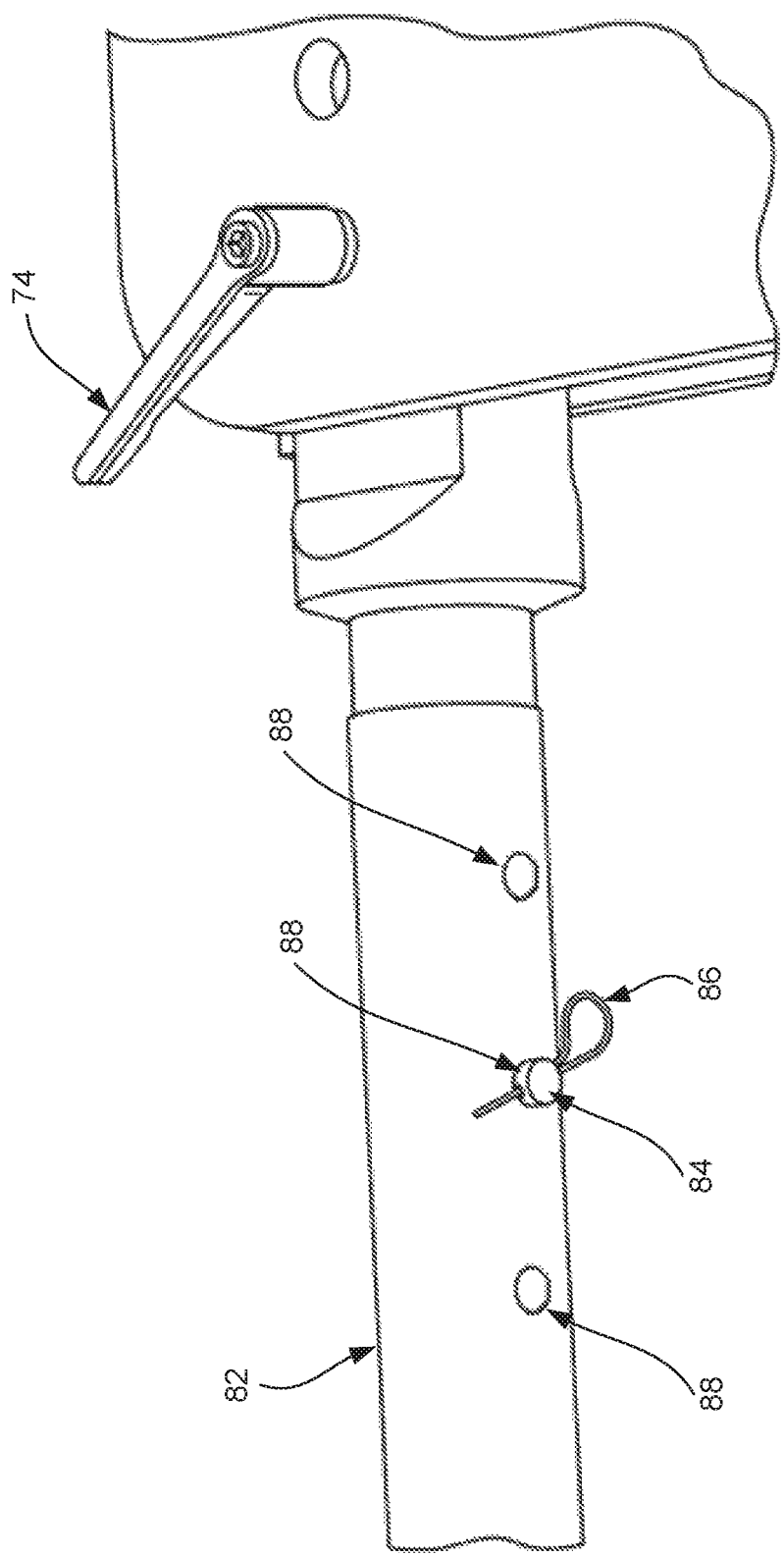
FIG. 27 illustrates telescoping horizontal beam using a clevis pin in accordance with one or more embodiments of the present technology.

FIG. 27 illustrates telescoping horizontal beam 82 using a clevis pin 84 similar to that described above with respect to FIG. 12, A telescoping horizontal beam 82 using a clevis pin 84 which allows for adjusted length of the frame with respect to the surgical table. The beam 82 can be adjusted among various discrete length configurations by moving clevis pin 84 between a plurality of adjustment apertures 88. In some embodiments, the clevis pin 84 is retained in position with a cotter pin 86. Locking handle 74, described above with respect to FIG. 25, may also be provided to lock the adduction angle of beam 82.

Figure 28:
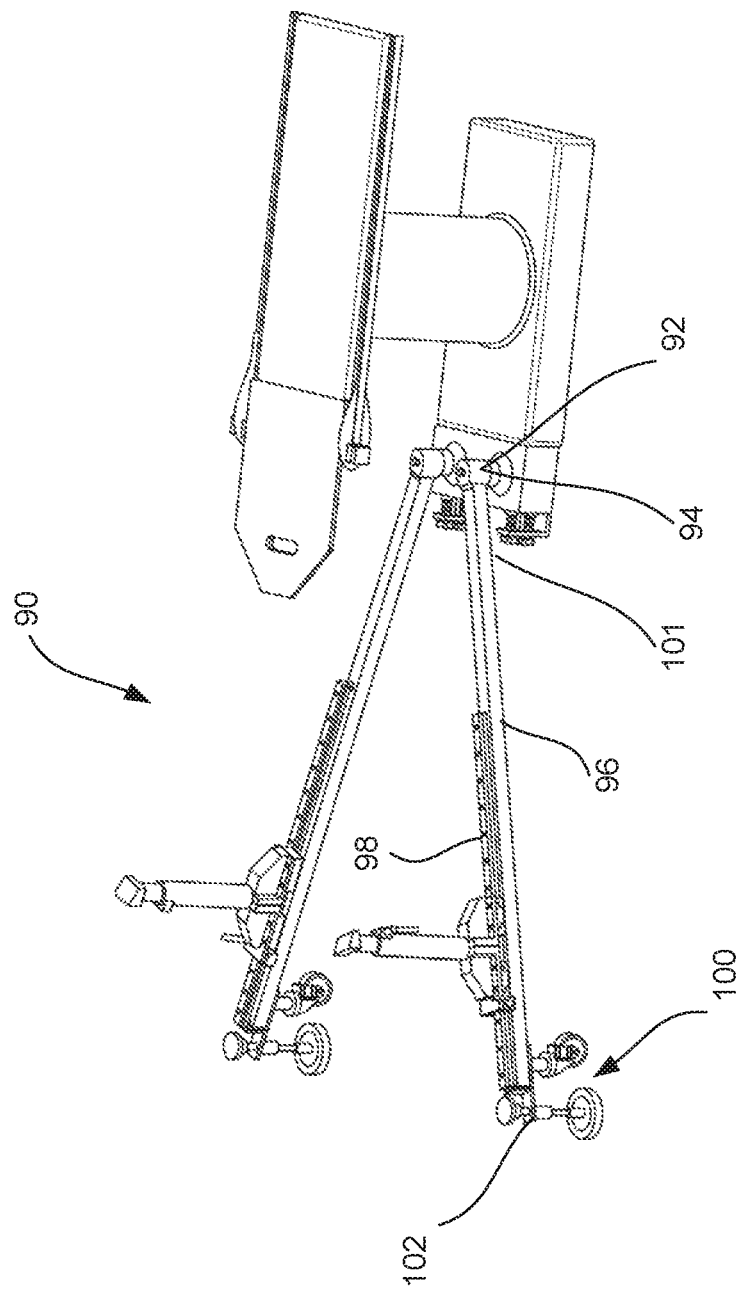
FIG. 28 is an isometric view of a frame design in accordance with one or more embodiments of the present technology.
Figure 29:
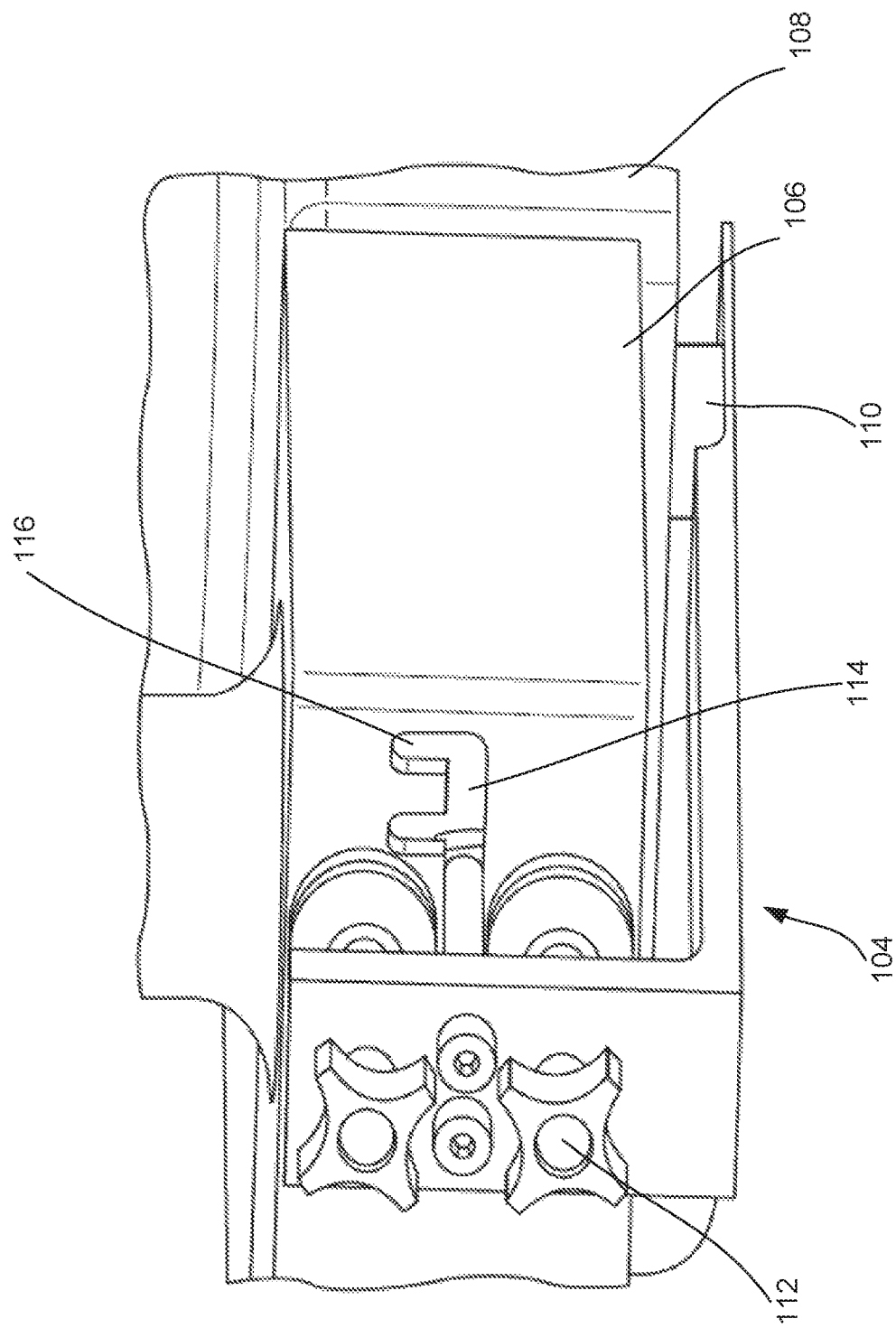
FIG. 29 illustrates an anchoring bracket that can be used to secure a base of a distraction system to a surgical table in accordance with one or more embodiments of the present technology.

FIG. 28 is an isometric view of a distraction system 90 in accordance with another representative embodiment of the present technology. The distraction system 90 integrates roller bearings 92 into the abduction joint 94 and uses a single steel square arm tube 96 to mount the rail 98. Each arm 96 rotates about an associated vertically oriented axis corresponding to the axis of bearing 92, to provide for hip adduction and abduction of a patient's leg. The rail 98 is mounted to the top portion of the square tube 96 to allow for gross traction. The joint 94 is located at a proximal end 101 of arm 96 and a caster and leveling foot assembly 100 supports the distal end 102 of the square tube 96. Distraction system 90 is shown attached to a surgical table, and may be used in conjunction with any suitable surgical table as described herein with respect to other embodiments of the present technology FIG. 29 illustrates an anchoring bracket 104 that can be used to secure a base 106 of the distraction system 90 to a surgical table 108 in accordance with one or more embodiments of the present technology. The feet 110 of the surgical table 108 secure the bracket 104 to the floor; then leveling screws 112 cause compression between base 106 and the surgical table 108. Horizontal and vertical slots 114 and 116, respectively, allow the bracket 104 to be maneuvered under the feet 110 of the surgical table 108 and/or lifted off the ground when the table is rolling or otherwise being repositioned. Bracket 104 is also shown attached to table 108 in FIG. 30.

Figure 30:
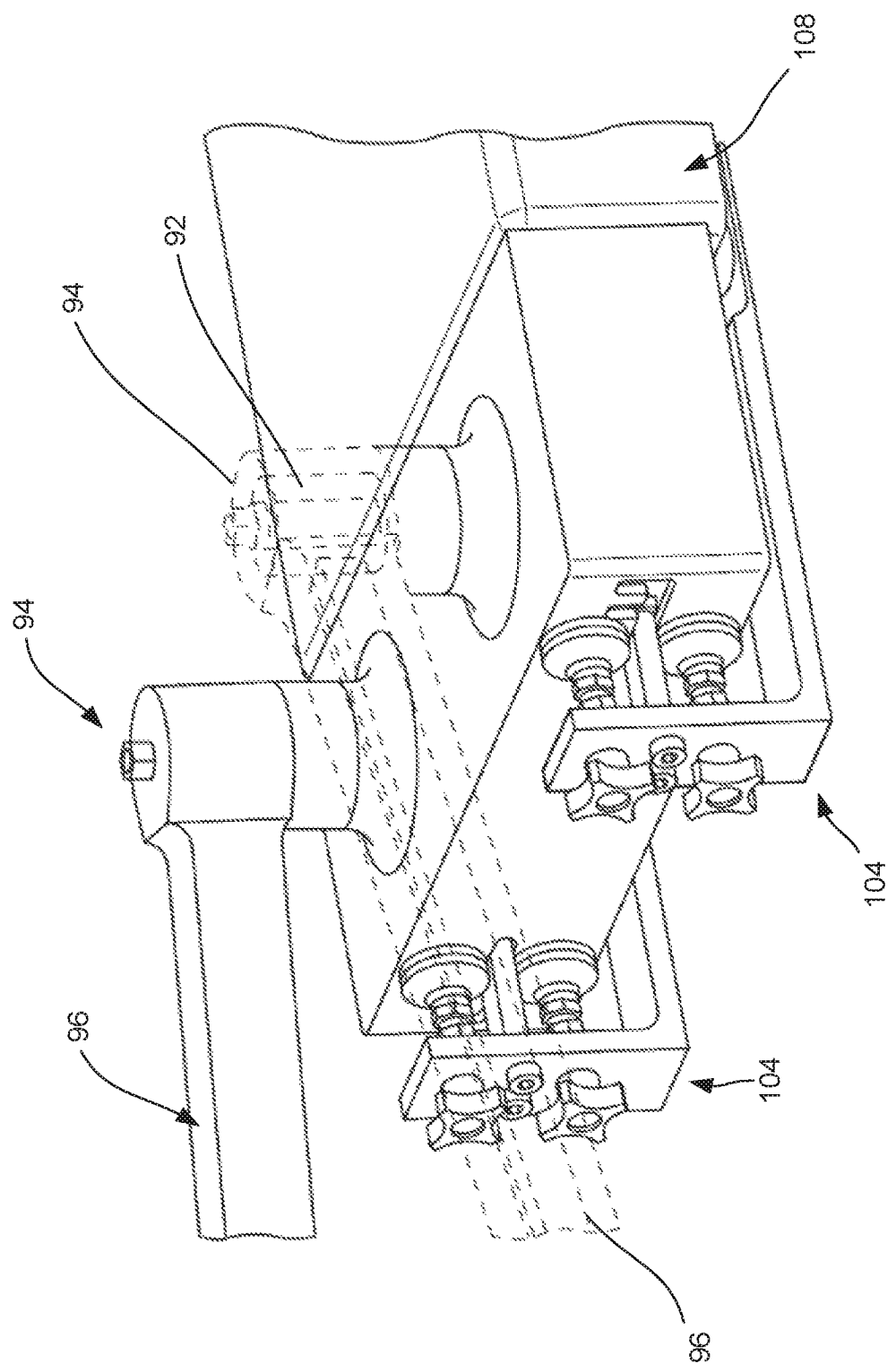
FIG. 30 illustrates an abduction joint with integrated roller bearing in accordance with one or more embodiments of the present technology.

FIG. 30 illustrates an abduction joint 94 with integrated roller bearing 92 in accordance with one or mare embodiments of the present technology. The roller bearing 92 is integrated into the abduction joint 94 in order to allow for smooth motion and to prevent torsional loads from deflecting the arm 96. The bearing 92 withstands the lifting moment produced when the patient's leg is in traction and therefore maintains the stability of the frame.

Figure 31:
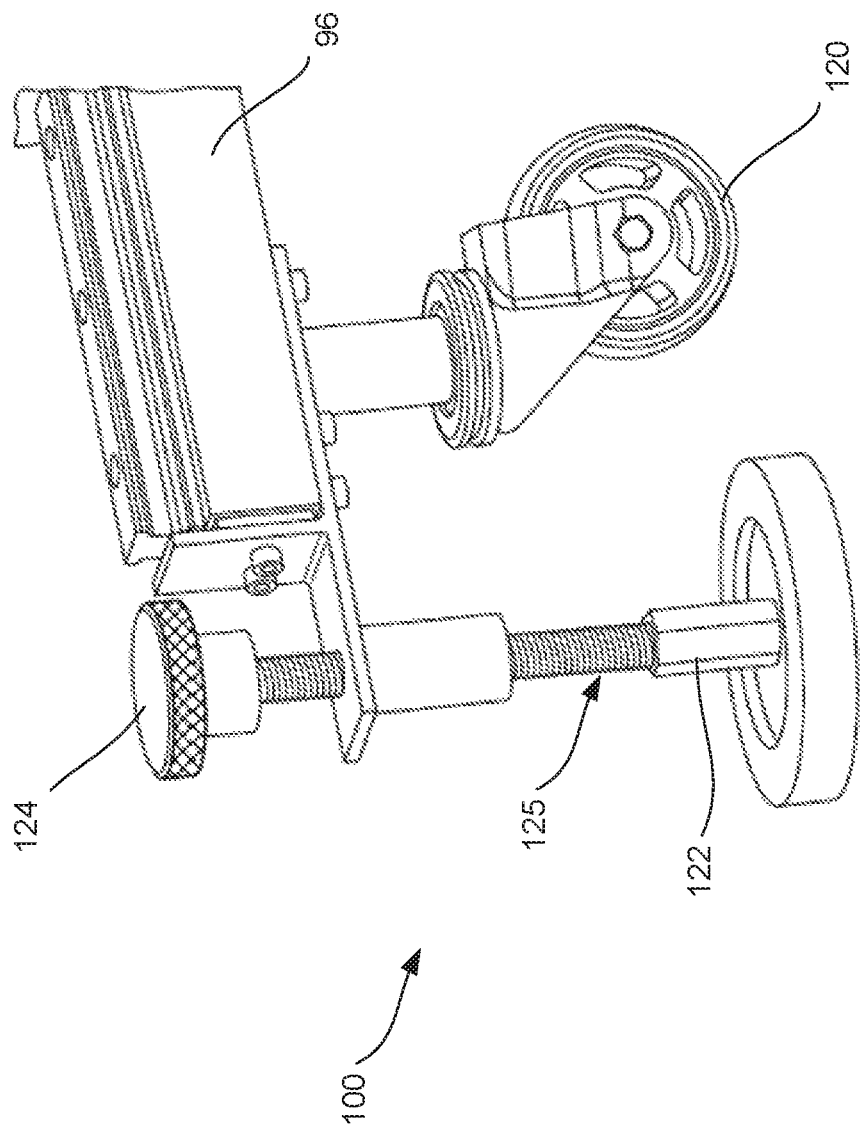
FIG. 31 illustrates a caster and leveling foot assembly of a distraction system that can be used in accordance with one or more embodiments of the present technology.

FIG. 31 illustrates the caster and leveling foot assembly 100 of the distraction system 90 (FIG. 28) that can be used in accordance with one or more embodiments of the present technology. A caster 120 and leveling foot 122 provide for both motion of the arm 96 about the abduction joint and also stability when the leveling foot 122 is lowered by actuation of jack screw 125 via adjuster knob 124.

Methods related to distracting the hip joint are also disclosed, such as a method for distracting the hip joint where the force resisting the distraction force is applied not through the use of a perineal post but through a combination of: 1) tilting the patient backward at an angle between 2 degrees and 20 degrees from the horizontal; and 2) placing fabric or material that produces increased frictional resistance between the patient's back and the underlying bed.

In an embodiment, a method for distracting a patient's hip joint includes applying a distraction force to the patient's leg and resisting the distraction force without the use of a perineal post. The resisting can include tilting the patient backward on a support surface relative to the patient's leg at an angle between 2 degrees and 20 degrees from horizontal and placing a friction increasing material between the patient and the support surface. In some embodiments, the method further comprises tilting the support surface to a contra-lateral side relative to the patient's leg at an angle between 0.5 and 2 degrees from horizontal.

In another representative embodiment, a method of configuring a surgical table as a distraction system includes attaching a distraction system base to a base portion of the surgical table and rotatably coupling a pair of arms to the distraction system base. The method can also include attaching a table extension to a table portion of the surgical table and positioning a friction pad on the table extension. In some embodiments, the table portion is tilted away from the distraction system base at an angle between 2 degrees and 20 degrees from horizontal. In some embodiments, each arm rotates about an associated vertically oriented axis. In some embodiments, the method includes connecting an upwardly extending support post to each of the pair of arms and/or tilting the table portion toward a lateral side of the surgical table at an angle between 0.5 and 2 degrees from horizontal.

The above description and drawings are illustrative and are not to be construed as limiting. Numerous specific details are described to provide a thorough understanding of the disclosure. However, in some instances, well-known details are not described in order to avoid obscuring the description. Further, various modifications may be made without deviating from the scope of the embodiments. Accordingly, the embodiments are not limited except as by the appended claims.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments. The features of the various embodiments of the present technology disclosed herein may be used in any combination or permutation, unless explicitly specified otherwise. For example, various linear-motion devices shown and described in the present disclosure may be utilized in any combination at the various linear-motion junctions between structures, as required or desired for any particular application of the present technology.

The terms used in this specification generally have their ordinary meanings in the art, within the context of the disclosure, and in the specific context where each term is used. It will be appreciated that the same thing can be said in more than one way. Consequently, alternative language and synonyms may be used for any one or more of the terms discussed herein, and any special significance is not to be placed upon whether or not a term is elaborated or discussed herein. Synonyms for some terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification. Unless otherwise defined, all technical and scientific terms used herein have the same meaning as commonly understood by one of ordinary skill in the art to which this disclosure pertains. In the case of conflict, the present document, including definitions, will control,

What is claimed is:

1. A method for stabilizing a patient on a patient support, the method comprising:
    positioning a friction-increasing pad on a surface of the patient support, wherein the patient support is capable of tilting cephalid-side down;
    positioning the patient at least partially on the friction-increasing pad; and
    tilting the patient support cephalid-side down so that the patient is inclined at an angle and applying a distraction force to a leg of the patient, wherein the distraction force is great enough to distract the hip joint;
    wherein the combination of (i) the friction force provided by the friction-increasing pad, and (ii) the force of gravity provided from tilting the patient support cephalid-side down during distraction provides a resistive force that opposes the distraction force being applied to the leg of the patient so as to keep the patient from sliding in the direction of the distraction without the use of a perineal post.

2. A method according to claim 1 wherein the patient is tilted on the patient support cephalid-side down so that the patient is inclined at an angle of 2-20 degrees from the horizontal.

3. A method according to claim 2 wherein the friction-increasing pad is disposed under at least one of the lower back and the buttocks of the patient.

4. A method according to claim 2 wherein the friction-increasing pad is disposed under at least a portion of the torso of the patient.

5. A method according to claim 2 wherein the friction-increasing pad comprises a foam pad.

6. A method according to claim 2 wherein the friction-increasing pad has a coefficient of friction greater than or equal to 0.52 as measured between human skin and a surface of the friction-increasing pad.

7. A method according to claim 2 wherein the friction-increasing pad has a coefficient of friction between 0.33 and 2.42 as measured between human skin and a surface of the friction-increasing pad.

8. A method according to claim 2 further comprising:
after applying a distraction force to a leg of the patient, performing a procedure on the patient.

9. A method according to claim 2 further comprising:
tilting the patient support toward a lateral side of the patient at an angle of between 0.5-2 degrees from the horizontal.

10. A method according to claim 9 wherein the friction-increasing pad provides resistance to sliding during lateral tilting.

11. A method according to claim 9 wherein the friction-increasing pad provides sufficient resistance to sliding to keep the patient from moving laterally during lateral tilting.

12. A method according to claim 1 wherein the friction-increasing pad is disposed so as to reside under the lower back and the buttocks of the patient.

13. A method according to claim 1 wherein the patient support comprises a surgical table and a table extension removably attached to the surgical table, and further wherein at least a portion of the friction-increasing pad is positioned on at least a portion of the table extension.

14. A method according to claim 13 wherein the portion of the friction-increasing pad positioned on the portion of the table extension is configured to reside under the buttocks of the patient.

15. A method according to claim 14 wherein at least a portion of the table extension is radiolucent.

16. A method for stabilizing a patient on a patient support, the method comprising:
positioning a friction-increasing pad on a surface of the patient support, wherein the patient support is capable of tilting cephalid-side down;
positioning the patient at least partially on the friction-increasing pad; and
tilting the patient support cephalid-side down so that the patient is inclined at an angle and applying a distraction force to a leg of the patient, wherein the distraction force is great enough to distract the hip joint;
wherein the combination of (i) the friction force provided by the friction-increasing pad, and (ii) the force of gravity provided from tilting the patient support cephalid-side down during distraction prevents the patient from sliding in the direction of the distraction without the use of a perineal post.

17. A method according to claim 16 wherein the patient is tilted on the patient support cephalid-side down so that the patient is inclined at an angle of 2-20 degrees from the horizontal.

18. A method according to claim 17 wherein the friction-increasing pad has a coefficient of friction between 0.33 and 2.42 as measured between human skin and a surface of the friction-increasing pad.

19. A method according to claim 16 wherein the patient support comprises a surgical table and a table extension removably attached to the surgical table, and further wherein at least a portion of the friction-increasing pad is positioned on at least a portion of the table extension.

20. A method for stabilizing a patient on a patient support, the method comprising:
positioning a friction-increasing pad on a surface of the patient support, wherein the patient support is capable of tilting cephalid-side down;
positioning the patient at least partially on the friction-increasing pad; and
tilting the patient support cephalid-side down so that the patient is inclined at an angle and applying a distraction force to a leg of the patient, wherein the distraction force is great enough to distract the hip joint;
wherein the coefficient of friction of the friction-increasing pad and the angle of tilt of the patient support are selected such that the combination of (i) the friction force provided by the friction-increasing pad, and (ii) the force of gravity provided from tilting the patient support cephalid-side down during distraction provides a resistive force that opposes the distraction force being applied to the leg of the patient so as to keep the patient from sliding in the direction of the distraction without the use of a perineal post.

21. A method according to claim 20 wherein the patient is tilted on the patient support cephalid-side down so that the patient is inclined at an angle of 2-20 degrees from the horizontal.

22. A method according to claim 21 wherein the friction-increasing pad has a coefficient of friction between 0.33 and 2.42 as measured between human skin and a surface of the friction-increasing pad.

23. A method according to claim 20 wherein the patient support comprises a surgical table and a table extension removably attached to the surgical table, and further wherein at least a portion of the friction-increasing pad is positioned on at least a portion of the table extension.

* * * * *